US008834864B2

(12) United States Patent
Odar et al.

(10) Patent No.: US 8,834,864 B2
(45) Date of Patent: *Sep. 16, 2014

(54) METHODS FOR REPAIRING AND REGENERATING HUMAN DURA MATER

(75) Inventors: Johann Odar, Muehlhausen (DE); Abolghassem Sepehrnia, Münster (DE); Ralph Schachtler, Wiesloch (DE); Axel W. Stemberger, Neubiberg (DE)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1078 days.

This patent is subject to a terminal disclaimer.

(21) Appl. No.: 11/291,336

(22) Filed: Dec. 1, 2005

(65) Prior Publication Data

US 2006/0167561 A1 Jul. 27, 2006

Related U.S. Application Data

(63) Continuation of application No. PCT/US2004/017910, filed on Jun. 4, 2004.

(60) Provisional application No. 60/475,995, filed on Jun. 5, 2003, provisional application No. 60/533,289, filed on Dec. 30, 2003.

(51) Int. Cl.
*A61K 35/12* (2006.01)
*C12N 11/02* (2006.01)
*A61L 27/36* (2006.01)
*A61L 27/24* (2006.01)

(52) U.S. Cl.
CPC ............ *A61L 27/3675* (2013.01); *A61L 27/24* (2013.01)
USPC ........................................ 424/93.7; 435/177

(58) Field of Classification Search
USPC ........................................ 424/93.7; 435/177
See application file for complete search history.

(56) References Cited

U.S. PATENT DOCUMENTS

| | | | |
|---|---|---|---|
| 2,507,244 A | 5/1950 | Correll | |
| 2,558,395 A | 6/1951 | Studer | |
| 4,013,078 A | 3/1977 | Field | |
| 4,124,705 A | 11/1978 | Rothman et al. | |
| 4,164,559 A | 8/1979 | Miyata et al. | |
| 4,179,400 A | 12/1979 | Tsao et al. | |
| 4,265,233 A | 5/1981 | Sugitachi et al. | |
| 4,291,013 A | 9/1981 | Wahlig et al. | |
| 4,292,972 A | 10/1981 | Pawelchak et al. | |
| 4,298,598 A | 11/1981 | Schwarz et al. | |
| 4,300,494 A | 11/1981 | Graiff et al. | |
| 4,347,234 A | 8/1982 | Wahlig et al. | |
| 4,362,567 A | 12/1982 | Schwarz et al. | |
| 4,377,572 A | 3/1983 | Schwarz et al. | |
| 4,424,208 A | 1/1984 | Wallace et al. | |
| 4,453,939 A | 6/1984 | Zimmerman et al. | |
| 4,482,386 A | 11/1984 | Wittwer et al. | |
| 4,515,637 A | 5/1985 | Cioca | |
| 4,536,387 A | 8/1985 | Sakamoto et al. | |
| 4,540,410 A | 9/1985 | Wood et al. | |
| 4,543,332 A | 9/1985 | Jao et al. | |
| 4,554,156 A | 11/1985 | Fischer | |
| 4,600,574 A | 7/1986 | Lindner et al. | |
| 4,640,834 A | 2/1987 | Eibl et al. | |
| 4,655,211 A | 4/1987 | Sakamoto et al. | |
| 4,746,514 A | 5/1988 | Warne | |
| 4,749,689 A | 6/1988 | Miyata et al. | |
| 4,803,075 A | 2/1989 | Wallace et al. | |
| 4,818,517 A | 4/1989 | Kwee et al. | |
| 4,832,686 A | 5/1989 | Anderson | |
| 4,837,285 A | 6/1989 | Berg et al. | |
| 4,891,359 A | 1/1990 | Saferstein et al. | |
| 4,925,677 A | 5/1990 | Feijen | |
| 4,946,870 A | 8/1990 | Partain, III. et al. | |
| 5,007,916 A | 4/1991 | Linsky et al. | |
| 5,017,229 A | 5/1991 | Burns et al. | |
| 5,023,082 A | 6/1991 | Friedman et al. | |

(Continued)

FOREIGN PATENT DOCUMENTS

| | | |
|---|---|---|
| EP | 0132983 A | 2/1985 |
| EP | 0376931 | 7/1990 |
| EP | 0132983 B2 | 12/1991 |
| EP | 0493387 | 7/1992 |
| EP | 0781564 A2 | 7/1997 |
| EP | 0891193 | 1/1999 |
| EP | 1 084 720 A1 | 3/2001 |
| EP | 01414370 B1 | 4/2007 |
| JP | 59-113889 | 6/1984 |
| JP | 05308969 | 11/1993 |

(Continued)

OTHER PUBLICATIONS

Cheung, David T., et al., "Mechanism of crosslinking of proteins by glutaraldehyde IV: In Vitro and In Vivo stability of a crosslinked collagen matrix", Connective Tissue Research, 1990;25(1), pp. 27-34.

(Continued)

*Primary Examiner* — Marcia S Noble
(74) *Attorney, Agent, or Firm* — Kilpatrick Townsend & Stockton LLP

(57) ABSTRACT

A method of using a substantially non-porous equine collagen foil to repair and regenerate dura mater tissue of mammals when the dura mater tissue is damaged as a result of injury, tumors, surgery, and the like. The non-porous equine collagen foil comprises collagen fibrils which provides a replacement dura mater composition that is elastic, liquid-tight, and which has a high tensile strength. The non-porous equine collagen foil is furthermore resorbable and provides a biomatrix, wherein a neodura is rapidly formed which becomes indistinguishable from the autologous dura mater in a matter of weeks. The process for making the equine collagen foil reduces the likelihood of disease transmission.

77 Claims, 22 Drawing Sheets

(56) References Cited

U.S. PATENT DOCUMENTS

| | | |
|---|---|---|
| 5,041,292 A | 8/1991 | Feijen |
| 5,061,274 A | 10/1991 | Kensey |
| 5,061,492 A | 10/1991 | Okada et al. |
| 5,080,893 A | 1/1992 | Goldberg et al. |
| 5,108,421 A | 4/1992 | Fowler |
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro |
| 5,162,430 A | 11/1992 | Rhee et al. |
| 5,165,938 A | 11/1992 | Knighton |
| 5,178,883 A | 1/1993 | Knighton |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,352,715 A | 10/1994 | Wallace et al. |
| 5,356,614 A | 10/1994 | Sharma |
| 5,384,333 A | 1/1995 | Davis et al. |
| 5,385,606 A | 1/1995 | Kowanko |
| 5,399,361 A | 3/1995 | Song et al. |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Allyne |
| 5,447,966 A | 9/1995 | Hermes et al. |
| 5,478,352 A | 12/1995 | Fowler |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A | 12/1996 | Yeung et al. |
| 5,595,735 A | 1/1997 | Saferstein et al. |
| 5,614,587 A | 3/1997 | Rhee et al. |
| 5,618,551 A | 4/1997 | Tardy et al. |
| 5,648,506 A | 7/1997 | Desai et al. |
| 5,667,839 A | 9/1997 | Berg |
| 5,672,336 A | 9/1997 | Sharma |
| 5,674,275 A | 10/1997 | Tang et al. |
| 5,690,675 A | 11/1997 | Sawyer et al. |
| 5,698,213 A | 12/1997 | Jamiolkowski et al. |
| 5,714,370 A | 2/1998 | Eibl et al. |
| 5,853,749 A | 12/1998 | Hobbs |
| 5,874,500 A | 2/1999 | Rhee et al. |
| 5,902,832 A | 5/1999 | Van Bladel et al. |
| 5,908,054 A | 6/1999 | Safabash et al. |
| 5,931,165 A | 8/1999 | Reich et al. |
| 5,997,895 A | 12/1999 | Narotam et al. |
| 6,063,061 A | 5/2000 | Wallace et al. |
| 6,066,325 A | 5/2000 | Wallace et al. |
| 6,110,484 A | 8/2000 | Sierra |
| 6,129,761 A | 10/2000 | Hubbell |
| 6,166,130 A | 12/2000 | Rhee et al. |
| 6,179,872 B1 | 1/2001 | Bell et al. |
| 6,277,394 B1 | 8/2001 | Sierra |
| 6,312,474 B1 | 11/2001 | Francis et al. |
| 6,312,725 B1 | 11/2001 | Wallace et al. |
| 6,328,229 B1 | 12/2001 | Duronio et al. |
| 6,440,167 B2 | 8/2002 | Shimizu |
| 6,458,386 B1 | 10/2002 | Schacht et al. |
| 6,458,889 B1 | 10/2002 | Trollsas |
| 6,624,245 B2 | 9/2003 | Wallace et al. |
| 6,706,690 B2 | 3/2004 | Reich et al. |
| 7,320,962 B2 | 1/2008 | Reich et al. |
| 7,435,425 B2 | 10/2008 | Qian et al. |
| 7,547,446 B2 | 6/2009 | Qian et al. |
| 7,871,637 B2 | 1/2011 | Qian et al. |
| 2001/0016205 A1 | 8/2001 | Shimizu |
| 2002/0193448 A1 | 12/2002 | Wallace et al. |
| 2003/0064109 A1 | 4/2003 | Qian et al. |
| 2005/0142162 A1 | 6/2005 | Hunter et al. |
| 2006/0147492 A1 | 7/2006 | Hunter et al. |
| 2008/0085316 A1 | 4/2008 | Qian et al. |
| 2008/0091277 A1 | 4/2008 | Deusch et al. |
| 2008/0286376 A1 | 11/2008 | Qian et al. |
| 2010/0028309 A1 | 2/2010 | Odar et al. |
| 2010/0292717 A1 | 11/2010 | Petter-Puchner et al. |
| 2010/0318048 A1 | 12/2010 | Hoefinghoff et al. |

FOREIGN PATENT DOCUMENTS

| | | | |
|---|---|---|---|
| JP | 6-254148 | 9/1994 | |
| JP | 9-504719 | 5/1997 | |
| JP | 07090241 | 4/2007 | |
| KR | 10-1991-0007847 B1 | 10/1991 | |
| WO | WO 86/00912 | 2/1986 | |
| WO | WO 92/21354 | 12/1992 | |
| WO | WO 92/22252 | 12/1992 | |
| WO | WO 94/27630 A1 | 12/1994 | |
| WO | WO 95/12371 | 5/1995 | |
| WO | WO 95/15747 | 6/1995 | |
| WO | WO 96/04025 | 2/1996 | |
| WO | WO 96/06883 | 3/1996 | |
| WO | WO 96/10374 | 4/1996 | |
| WO | WO 96/10428 | 4/1996 | |
| WO | WO 96/14368 | 5/1996 | |
| WO | WO 96/39159 | 12/1996 | |
| WO | WO 97/37694 A1 | 10/1997 | |
| WO | WO 98/08550 A1 | 3/1998 | |
| WO | 99/13902 A1 | 3/1999 | |
| WO | 02/22184 A2 | 3/2002 | |
| WO | WO 02/070594 * | 9/2002 | ........... C08J 9/00 |
| WO | WO 03/007845 A1 | 1/2003 | |
| WO | WO 2006/031358 A | 3/2006 | |
| WO | WO 2006/118460 A1 | 11/2006 | |
| WO | WO 2007/001926 A2 | 1/2007 | |
| WO | WO 2008/016983 A2 | 2/2008 | |

OTHER PUBLICATIONS

Jonas, Richard A., et al., "A new sealant for knitted Dacron prostheses: Minimally cross-linked gelatin", J. Vasc. Surg., Mar. 1988;7(3), pp. 414-419.

Larson, Paul O., "Topical Hemostatic Agents for Dermatologic Surgery", J. Dermatol. Surg. Oncol., Jun. 1988;14(6), pp. 623-632.

McPherson, J. M. et al., "An examination of the biologic response to injectable, glutaraldehyde cross-linked collagen implants", J. Biomed. Mater. Res., Jan. 1986;20(1), pp. 93-107.

McPherson, J. M., et al., "The preparation and physiochemical characterization of an injectable form of reconstituted, glutaraldehyde cross-linked, bovine corium collagen", J. Biomed. Mater. Res., Jan. 1986;20(1), pp. 79-92.

McPherson, John M., et al., "The Effects of Heparin on the Physiochemical Properties of Reconstituted Collagen", Coll. Relat. Res., Jan. 1988;8(1), pp. 65-82.

Nimni, M. E., et al., "Chemically modified collagen: A natural biomaterial for tissue replacement", J. Biomed. Mater. Res., Jun. 1987;21(6), pp. 741-771.

Nimni, Marcel E., "The cross-linking and structure modification of the collagen matrix in the design of cardiovascular prosthesis", J. of Cardiac Surgery, Dec. 1988;3(4), pp. 523-533.

Rosenblatt, Joel, et al., "Effect of electrostatic forces on the dynamic rheological properties of injectable collagen biomaterials", Biomaterials, 1992;13(12), pp. 878-886.

(56) References Cited

OTHER PUBLICATIONS

Rosenblatt, Joel, et al., "Injectable collagen as a pH-sensitive hydrogel", Biomaterials, Oct. 1994;15(12), pp. 985-995.
Rossler, B., et al., "Collagen microparticles: preparation and properties", J. Microencapsulation, Jan.-Feb. 1995;12(1), pp. 49-57.
Wallace, Donald G., et al., "Injectable cross-linked collagen with improved flow properties", J. of Biomedical Materials Research, Aug. 1989;23(8), pp. 931-945.
Wallace, Donald, "The relative contribution of electrostatic interactions to stabilization of collagen fibrils", Biopolymers, May-Jun. 1990; 29(6-7), pp. 1015-1026.
Barrow, D.L., et al.; "The Use of Greater Omentum Vascularized Free Flaps for Neurosurgical Disorders Requiring Reconstruction", *J. Neurosurg.*; vol. 60; pp. 305-311 (Feb. 1984).
Baxter product brochure for TissuFleece E, TissuCone E and TissuFoil E (2003).
Baxter Product Catalogue; Collagen; 4 pages (2006).
Chaplin, J.M., et al.; "Use of an Acellular Dermal Allograft for Dural Replacement: An Experimental Study"; *Neurosurgery*; vol. 45;2; pp. 320-327 (Aug. 1999).
Collins, R.L.L., et al.; "Use of Collagen Film as a Dural Substitute: Preliminary Animal Studies"; *Journal of Biomedical Materials Research*; vol. 25; pp. 267-276 (1991).
European Search Report for EP 04 25 3332, Aug. 31, 2004.
Filippi, R., et al.; "Bovine Pericardium for Duraplasty: Clincal Results in 32 Patients"; *Neurosurg. Rev.*; vol. 20; pp. 103-107 (2001).
Kline, D.G.; "Dural Replacement with Resorbable Collagen"; *Arch Surg*; vol. 91; pp. 924-929 (Dec. 1965).
Laquerriere, A., et al.; "Experimental Evaluation of Bilayered Human collagen as a Dural Substitute"; *J. Neurosurg*; vol. 78; pp. 487-491 (Mar. 1993).
Lee, J.F., et al.; "Experimental Evaluation of Silicon-Coated Dacron and Collagen Fabric-Film Laminate as Dural Substitutes"; *J. Neurosurg.*; vol. 27; pp. 558-564 (Apr. 1967).
Matsumoto, K., et al.; "A Gelatin Coated Collagen-Polyglycolic Acid Composite Membrane as a Dural Substitute": *ASAIO Journal*; pp. 641-645 (2001).
Maurer, P.K., et al.; "Vicryl (Polyglactin 910) Mesh as a Dural Substitute"; *J Neurosurg*; vol. 63; pp. 448-452 (Sep. 1985).
Meddings, N., et al.; "Collagen Vicryl—A New Dural Prosthesis"; *Acta Neurochir*; vol. 117 ; pp. 53-58 (1992).
Mello, L.R., et al.; "Duraplasty with Biosynthetic Cellulose: An Experimental Study"; *J Neurosurg*; vol. 86; pp. 143-150 (Jan. 1997).
Narotam, P.K. et al.; "Experimental Evaluation of Collagen Sponge as a Dural Graft"; *British Journal of Neurosurgery*; vol. 7; pp. 635-641 (1993).
Narotam, P.K. et al.; "A Clinicopathological Study of Collagen Sponge as a Dural Graft in Neurosurgery"; *J Neurosurg*; vol. 82; pp. 406-412 (Mar. 1995).
O'Neill, P., et al.; "Use of Porcine Dermis as Dural Substitute in 72 Patients"; *J. Neurosurg.*; vol. 61; pp. 351-354 (Aug. 1984).
Palm, S.J., et al.; "Dural closure with Nonpenetrating Clips Prevents Meningoneural Adhesions: An Experimental Study in Dogs"; *Neurosurgery*; vol. 45:4; pp. 875-882 (Oct. 1999).
Parizek, J., et al.; "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery"; *Acta Neurochir*; vol. 139; pp. 827-838 (1997).
Park, Y-K., et al.; "Prevention of Arachnoiditis and Postoperative Tethering of the Spinal Cord with Gore-Tex Surgical Membrane: An Experimental Study with Rats"; *Neurosurgery*; vol. 42 :4; pp. 813-824 (Apr. 1998).
Pietrucha, K.; "New Collagen Implant as Dural Substitute"; *Biomaterials*; vol. 12; pp. 320-323 (Apr. 1991).
Raul, J.S., et al.; "Utilisation du Polyester Urethane (NEURO-PATCH®) Comme Substitut Dural"; *Neurochirugie*; vol. 49:2-3; pp. 83-89 (2003).

Reddy, M., et al.; "A Clinical Study of a Fibrinogen-Based Collagen Fleece for Dural Repair in Neurosurgery"; *Acta Neurochir*; vol. 144; pp. 265-269 (2002).
San-Galli, F., et al.; "Experimental Evaluation of a Collagen-Coated Vicryl Mesh as a Dural Substitute"; *Neurosurgery*; vol. 30:3; pp. 396-401 (1992).
Shaffrey, C.I., et al.; "Neurosurgical Applications of Fibrin Glue: Augmentation of Dural Closure in 134 Patients"; *Neurosurgery*; vol. 26:2; pp. 207-210 (1990).
Smith, K.A., et al.; "Delayed Postoperative Tethering of the Cervical Spinal Cord"; *J Neurosurg*; vol. 81; pp. 196-201 (Aug. 1994).
Springorum, H.W.; "Die Verwendung von Kollagenfolien zur Uberbruckung von Defekten des Gleitgewebes bei Achillotenotomien und Achillessehnenrupturen"; *Akt. Traumatol*; vol. 15; pp. 120-121 (1985).
Stricker, A., et al.; "Die Verwendung von TissuFoil Membran bei der Sinusbodenaugmentation"; *Ellipse*; vol. 17:1; pp. 1-5 (2001).
Viñas, F.C., et al.; "Evaluation of Expanded Polytetrafluoroethylene (ePTFE) versus Polydioxanone (PDS) for the Repair of Dura Mater Defects"; *Neurological Research*; vol. 21; pp. 262-268 (Apr. 1999).
Warren, W.L., et al.; "Dural Repair Using Acellular Human Dermis: Experience with 200 Cases: Technique Assessment"; *Neurosurgery*; vol. 46:6; pp. 1391-1396 (Jun. 2000).
Ziegelaar, B.W.; "Tissue Engineering of a Tracheal Equivalent"; Doctoral Thesis at Ludwig Maximilians University, Munich, Germany: 25 pages (2004).
Ansell et al., "Gelfoam and Autologous Clot Embolization: Effect on Coagulation", *Invest. Radiol.* (1978) 13:115-120.
Barton et al., "Fibrin Glue as a Biologic Vascular Patch—A Comparative Study" (abstract posted at http://www.ncbi.nlm.nih.gov/ on Jan. 3, 2001 from) *J. Surg. Res.* (1986) 40(5): 510-513.
Boyers et al., "Reduction of Postoperative Pelvic Adhesions in the Rabbit with Gore-Tex Surguical Membrane" *Fert. Ster.* (1988) 49(6):1066-1070.
Bruck, S. D., ed., Controlled Drug Delivery, CRC Press, Boca Raton, FL (1983) A title page and table of contents.
Cantor et al., "Gelfoam and Thrombin in Gastrointestinal Bleeding: An Experimental Study", pp. 890-893, 1950.
Cantor et al., "Gelfoam and Thrombin in Treatment of Massive Gastroduodenal Hemmorhage: A Preliminary Report" *Am J. Surg.* (1950) pp. 883-887.
Cantor et al., "Gelfoam and Thrombin in Treatment of Massive Upper Gastroduodenal Hemorrhage", *Am. J. Surg.* (1951) pp. 230-235.
Chuang et al., "Sheath Needle for Liver Biopsy in High-Risk Patients". *Radiology* (1988) 166:261-262.
Collins et al., "Enemata of Gelfoam-Milk Suspension Combined with Thrombin Solution to Control Massive Hemorrhage Following Anorectal Surgery", *Am. J. Proctol.* (1951) 2:60-63.
Edgerton et al., "Vascular Hamartomas and Hemangiomos: Classification and Treatment" *Southern Med. J.* (1982) 75(12):1541-1547.
Heller et al., "Release of Norethindrone from Poly(Ortho Esters)" *Polymer Engineering Sci.* (1981) 21:727-731.
Hood et al., "Efficacy of Topical Hemostat Floseal Matrix in Vascular Surgery," 24th World Congress of the International Society for Cardiovascular Surgery (Sep. 12-16, 1999) 2 pages total.
Hotz et al., "collagen and Fibrin as Biologic Binders from Granular Hydroxyapatite" (abstract posted at http://www.ncbi.nlm.nih.gov/ on Jan. 3, 2001 from) *Dtsh. Z. Mund. Kiefer Geichtshir.* (1989) 13(4):296-300.
Jeong et al., "Biodegradable Block Copolymers as Injectible Drig-Delivery Systems" *Nature* (1997) 388:860-862.
Krill et al., "Topical Thrombin and Powdered Gelfoam: An Efficiaent Hemostatic Treatment for Surgery", *J. Tenn. Dent. Assoc.* (1986) 66(2):26-27.
Langer et al., "Chemical and Physical Structure of Polymems as Carriers for Controlled Release of Bioactive Agents: A Review" *Rev. Marco Chem. Phys.* (1983) C23(1):61-126.
Leong et al., "Polyanhydrides for Controlled Release of Bioactive Agents" *Biomaterials* (1986) 7:364-371.
Leong et al., "Polymeric Controlled Drug Delivery" *Adv. Drug Delivery Rev.* (1987)1:199-233.
Maok, "Hemostatic Agents" (1991) *Today's O.R. Nurse*, pp. 6-10.

(56) References Cited

OTHER PUBLICATIONS

Masar et al., "Synthesis of Polyurethanes and Investigation of their Hydrolytic Stability" *J. Polymer. Sci.*, Polymer Symposium (1979) 66:259-268.

McClure et al., "Massive Gastroduodenal Hemorrhage: Treatment with Powdered Gelfoam and Buffered Thrombin Solution" *Surg.* (1952) 32:630-637.

PCT International Preliminary Report on Patentability and Written Opinion mailed Feb. 17, 2009, International Application No. PCT/US2007/074984, 8 pages.

Pitt et al., "Controlled Release of Bioactive Materials". R. Baker, Ed., Academic Press. New York. 1980.

Riley et al., "Percutaneous Liver Biopsy with Plugging of Needle Track: A Safe Method for Use in Patients with Impaired Coagulation" *Lancet* (Aug. 25, 1984) pp. 436.

Sidman et al., "Biodegradable, Implantable Sustained Release Systems Based on Glutamic Acid Copolymers" *J. Membrane Science* (1979) 7:227-291.

Sugitachi et al., "A Newly Devised Chemo-embolic Agent, G.T. XIII-ADM." (English abstract posted at http://www.ncbi.nlm.nih.gov/ on Jan. 3, 2001 from) *Gan. To. Kagaku Ryoho.* (1985) 12(10) 1942-1943.

Sugitashi et al., "Locoregional Therapy in Patients with Maignant Pleural Effusion—Two Different Kinds of BAC Therapy" (English abstract posted at http://www.ncbi.nlm.nih.gov/ on Jan. 3, 2001 from) *Gan. To. Kagaku Ryoho.* (1992) 19(10):1640-1643.

Sugitachi et al., "Preoperative Transcatheter Arterial Chemo-embolization for Locally Advanced Breast Cancer: Application for New Thrombotic Materials" *Japan J. Surg.* (1983) 13(5):456-458.

Tobin et al., "Plugged Liver Biopsy in Patients with Impaired Coagulation" *Digestive Diseases and Science* (1989) 34(1):13-15.

Tucker et al., "Absorbable Gelatin (Gelfoam) Sponge" Charles T. Thomas, Publisher, Springfiled, Illinois, 3-125, 1965.

Vander Salm et al., "Reduction of Sternal Infection by Application of Topical Vancomycin" *J. Thorac. Sur.* (1989) 98:618-622.

Yuki et al., "Effects of EndoscopicVariceal Sclerotherapy using GT XIII on Blood Coagulation Tests and the Renal Kallikrein-kinin System" (English abstract posted at http://www.ncbi.nlm.nih.gov/ on Jan. 3, 2001 from) *Gastroentral. Japan* (1990) 25(5):561-567.

Zins et al., "US-Guided Percutaneous Liver Biopsy with Plugging of the Needle Track: A Prospective Study in 72 High-Rish Patients" *Radiology* (1992) 184(3):841-843.

\* cited by examiner

METHODS FOR REPAIRING AND REGENERATING HUMAN DURA MATER

CROSS-REFERENCE TO RELATED APPLICATIONS

This is a continuation application of International Application No. PCT/US2004/017910 filed on Jun. 4, 2004, which claims priority to U.S. Provisional Application Nos. 60/475,995 filed on Jun. 5, 2003, and 60/533,289 filed on Dec. 30, 2003.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to the use of substantially non-porous collagen foil compositions as graft material to repair and/or regenerate dura mater tissue of mammals. More particularly, the present invention relates to the use of collagen foil compositions of a non-human origin as substitute dura mater material and as a biomatrix for dura regeneration.

BACKGROUND OF THE INVENTION

The dura mater is a functionally significant structure in the anatomy of the central nervous system, forming a membrane system which envelops the entire central nervous system and protects it from external influences.

The dura mater may require repair due to a number of causes, including trauma, inflammatory or neoplastic processes, surgical procedures, or congenital abnormalities. The need to close dural defects, especially following surgical procedures and in the presence of posttraumatic fistulae, has prompted a quest for the ideal dura mater substitute. These defects may result in postoperative complications, in particular, seepage of cerebrospinal fluid, infections, and resultant cerebral seizures. Some form of dural graft procedure is required in association with almost 30% of craniotomies. As the primary closure of the dural defect often fails, the availability of a dural substitute to avoid the above complications is of great practical significance.

A permanent liquid-tight closure of the dura mater is required to avoid cerebrospinal fluid leakage after skull injuries or surgical interventions to remove malignant tumors in the brain or spinal column. Neurosurgeons currently use resorbable or non-resorbable dura mater substitutes and usually attach them to the dura mater in the cranium or spinal column with sutures and/or fibrin glue. Examples of resorbable materials have included human cadaveric dura mater, human fascia lata, bovine pericardium, xenogen collagen-sponges, and implants from woven materials, consisting of resorbable polyester (polyglactin and/or poly-p-di-oxanon). Examples of non-resorbable dura substitutes include materials made of poly-tetra-fluoro-ethylene (PTFE) or polyester urethane.

Almost all dural grafts studied to date are associated with complications, some major. The main complications that have been reported are chronic inflammatory and rejection reactions and the formation of corticomeningeal adhesions resulting among other things in the development of epileptogenic foci. Haematomas and cerebrospinal fluid fistulae are also observed, which in turn provide a point of entry for various-disease-causing organisms.

Numerous materials and methods have been evaluated over the past decades in quest of the ideal dural graft, including various metallics, implants, synthetic materials, autologous tissue transplants and preserved human cadaveric dura mater. Most of these products are unsuitable because of the associated postoperative complications, some of them serious. Examples of the complications include chronic inflammatory and rejection reactions, development of corticomeningeal adhesions, haemorrhages, and encapsulation of dura mater grafts in a thick layer of connective tissue. Previous studies on the subject of suitable dural replacements show that early graft absorption coupled with formation of an endogenous neodura are the main factors predictive of uneventful and permanent dural fusion.

Several autologous tissues have been used in the past as dura mater substitutes. In 1911, Kostling used a patient's hernial sac to form a dural graft. Kostling, W., *Med Wochenschr*, 58, 1042 (1911). Other autologous tissues such as temporal fascia, fascia lata femoris and periosteal flaps have been used since then. Barrow et al. successfully reconstructed a large dural lesion with endogenous greater omentum. Barrow et al., *J. Neurosurg.* 60; 305-1 (1987). The advantage of autologous grafts is that there is no risk of pathogen transmission or tissue rejection. However, the additional removal of tissue increases the surgical trauma and prolongs what is probably in any case a complicated surgical procedure.

Preserved human cadaveric dura has been used routinely for many years as a dura mater substitute for dural replacement in human subjects. These preparations consist of connective tissue fibres which are interwoven like the body's own dura mater. After the cadaveric human dura mater are utilized in neurosurgery, they are said to form a liquid-tight closure, similar to the body's own dura mater, and are eventually replaced by the body's own tissue during a degradation process over an extended period of time. The cadaveric-derived material is preserved by freeze-drying (lyophilization) and gamma sterilization (Lyodura, B. Braun Melsungen Aktiengesellschaft, Melsungen, Germany) or in a multistage chemical process (Tutoplast® process; Tutoplast® Dura, Tutogen Medical GmbH, Neunkirchen am Brand, Germany). Human cadaveric dura mater grafts, however, have been associated with significant risks in carrying viruses and prions, which can cause the feared disease spongiform encephalitis (Creutzfeldt-Jakob disease or Gerstmann Streussler syndrome). Due to numerous deaths occurring after implantation of human dura mater, the use of human cadaveric dura mater grafts has been restricted or banned in a number of countries.

Human fascia lata and pericardium preparations have also been used as dura mater substitute material with less danger of transmitting infectious agents than human cadaveric dura mater. While these preparations carry less risk of transmitting disease, they are resorbed slowly over periods of months or years which can result in scar formation and encapsulation of the dura substitute material.

Dura substitutes have also been derived from non-human sources such as bovine or porcine collagen isolated from skin or tendons and bovine pericardium tissue. Similar to human-derived sources, some bovine dura substitutes have been believed to transmit disease, namely bovine spongiform encephalopathy (BSE), to the patient receiving the dura mater graft. Use of porcine derived dural substitutes, however, resulted in adhesions with the underlying cerebral tissue.

Narotam et al., U.S. Pat. No. 5,997,895, disclose dural substitutes derived from treated xenogenic collagen in the forms of porous collagen sponge, felt, or film. The treatment of collagen inactivates viral and prion contamination such that the substitute does not contain infectious amounts of viruses and prions. Porosity of dura substitutes is disclosed as necessary to permit vessels, cells and meningeal tissue to infiltrate the dura substitute. In clinical practice, however, the application of the available porous materials is connected with disadvantages, since shape stability and primarily liquid tightness are not always guaranteed. Narotam et al. also disclose a dura substitute which is a sandwich of two or more forms of collagen sponge, felt, or film wherein at least one form is sufficiently porous for ingrowth of meningeal tissue.

Resorbable polyesters are also available for clinical use but have the disadvantage of low elasticity and slow degradation. In special situations these implants cause wound healing problems and may increase infection.

Foils or sheets consisting of a metal such as gold, platinum, silver, nickel, tantalum, or steel, or polymers such as polytetrafluoroethylene (PTFE) or other polyesters, have also been used as dura mater substitutes. These substitutes are not absorbed by the patient, however, but become encapsulated in a tough layer of connective tissue and remain in the body for the life of the patient as a foreign body without substitution by the body's own structures. This can result in a high risk of germ growth in the inner pores which cannot be controlled by the body's own defence mechanism, due to the porous structure of the PTFE foil membranes.

Collagen-based products are becoming increasingly popular. Chemical processes can be used to modify structures with a high connective tissue component, such as the pericardium or dermis, so that only an acellular, antigen-free collagen scaffold is preserved. Products are available which consist entirely of collagen fibrils or collagen-coated synthetic materials. In both cases the collagen fibre network acts as a matrix for growing endogenous connective tissue.

Chaplin et al. tested a product obtained from guinea pig skin (XenoDerm, Lifecell Corp., The Woodlands, Tex.) in an animal model. *Neurosurgery,* 45:2, 320-7 (August 1999). The comparator was autologous pericranium. The epidermis, all cellular components, and other potentially antigenic or infectious elements were chemically removed in the manufacturing process. The collagen fibres and structural architecture of the skin were preserved unchanged. The product was rapidly reported to incorporate with the surrounding dura in the presence of a mild cellular response. Invading fibroblasts were observed preferentially at the implantation site. The graft and original dura mater were said to be barely distinguishable at the end of the study 6 months postoperatively.

Following on from these results, Warren et al. (2000) investigated AlloDerm® (LifeCell Corp., The Woodlands, Tex.) for dural replacement in human subjects. *Neurosurgery* 46(6):1391-96 (2000). Two hundred patients received an AlloDerm dural graft during the study. This material is obtained from human dermis. The manufacturing process is said to be the same as for XenoDerm, producing an acellular collagen biomatrix that is major histocompatibility complex (MHC) antigen free. Seven of the 200 patients developed postoperative complications such as infection and cerebrospinal fluid (CSF) fistulae, but none of these incidents was reported as caused by the graft itself. Surgical revision was said to show that none of these patients had developed adhesions or rejection reactions at the dural graft site. The material was said to be highly similar to the surrounding dura on macroscopic examination. Long term study data on this product are not yet available.

Filippi et al. (2001) described experiments in the use of solvent preserved gamma sterilized bovine pericardium (Tutopatch®, Tutogen Medical GmbH, Neunkirchen, Germany) for dural replacement in 32 subjects. Filippi, et al., *Neurosurg. Rev.,* 24:103-107 (2001). The postoperative course was said to be uneventful in all but one patient, who died of cardiac causes shortly after the operation. The graft was described as easy to handle, durable and low-cost. Long term study data ruling out possible late complications are not yet available.

Collagen products are suitable for use as biomaterial on many accounts: the chemotactic interaction in which they engage facilitates rapid infiltration of endothelial cells and fibroblasts, which in turn produce and deposit new collagen fibres; a concomitant limited lymphocytic inflammatory response in surrounding structures promotes absorption of the collagen biomatrix. Collagen also possesses haemostatic properties which are put to therapeutic use. Platelets deposit themselves on the collagen structure, disintegrate and in doing so release clotting factors which facilitate fibrin formation in conjunction with plasma factors.

Known dura substitute materials and related methods of using such materials fail to provide a liquid-tight, resorbable substitute dura mater that avoids encapsulation, dura scar formation, or adhesion to cerebral tissue, and furthermore has a low risk of transmitting germs, viruses, and prions which can cause spongiform encephalitis or other diseases. An ideal dura mater replacement should not engender an immune defence response or inflammation and must be non-toxic. It should be rapidly absorbed and at the same time allow connective tissue architecture to build up so that an endogenous neodura develops. The graft should not adhere or fuse with cerebral tissue or bone during this process. The material should be resistant to tearing, keep its shape, and resist cerebrospinal fluid permeation. The replacement dura mater also should be stable in its volume and shape wherein it resists expansion or contraction after implantation. Other important criteria are viral and prion safety, user friendliness and economical manufacturing cost.

SUMMARY OF THE INVENTION

Among the various aspects of the present invention, therefore, is the provision of a replacement dura mater material that is resorbable, liquid-tight, elastic, stable in its volume and shape, and provides an excellent safety profile concerning the risk of disease transmission.

Briefly, therefore, the present invention relates to a method for repairing and/or regenerating dura mater tissue in a mammal. The dura mater tissue is contacted with an equine collagen foil comprising a biomatrix of collagen fibrils. The equine collagen foil is formed by a process wherein a suspension of collagen fibrils is precipitated to form the foil of collagen fibrils, and wherein the collagen fibrils are not cross-linked by chemicals or by radiation.

In another aspect, the invention relates to a method for repairing dura mater tissue in a mammal comprising contacting the dura mater tissue with a substantially non-porous equine collagen foil comprising a non-naturally occurring biomatrix of collagen fibrils, wherein the equine collagen foil consists essentially of acellular components, and wherein the collagen fibrils are not cross-linked by chemicals or radiation.

In another aspect, the invention relates to a method for repairing and/or regenerating dura mater tissue in a mammal comprising contacting the dura mater tissue with a substantially non-porous equine collagen foil consisting essentially of a collagen biomatrix wherein the collagen biomatrix is not cross-linked by chemicals or radiation.

Other aspects and features of this invention will be in part apparent and in part pointed out hereinafter.

DETAILED DESCRIPTION OF THE PREFERRED EMBODIMENTS

In accordance with the present invention, it has been surprisingly discovered that a substantially non-porous foil comprised of equine collagen fibrils in a non-naturally occurring biomatrix can be effectively utilized as a resorbable dura mater substitute for dura repair, regeneration, and restoration in mammals, including humans, laboratory animals, and the like. The equine collagen foil of the present invention is liquid-tight and provides high safety features against the risk of transmission of viruses or prions. In addition, the equine collagen foil is flexible and elastic in nature while maintaining a high tensile strength. This foil, hereinafter referred to as "equine collagen foil," when implanted, corresponds in important properties to the human dura mater. The equine collagen foil serves as a biomatrix scaffold for cellular ingrowth in vivo, and is replaced by a neodura during regeneration and restoration.

In one embodiment, the equine collagen foil biomatrix is comprised of connective tissue proteins consisting essentially of collagen fibrils. Preferably, the equine collagen foil biomatrix is comprised of connective tissue proteins consisting of collagen fibrils. More preferably, the equine collagen foil biomatrix is comprised of connective tissue proteins consisting of Type I collagen fibrils.

In addition to being comprised of collagen fibrils, the equine collagen foil can further comprise an excipient, a preservative, a growth factor, or an additive that aids in the flexibility and elasticity of the final product.

Equine Collagen Foil

The equine collagen foil of the present invention is a biomatrix of collagen fibrils treated to remove cellular components and to form a sheet of collagen fibrils.

Figure 1:
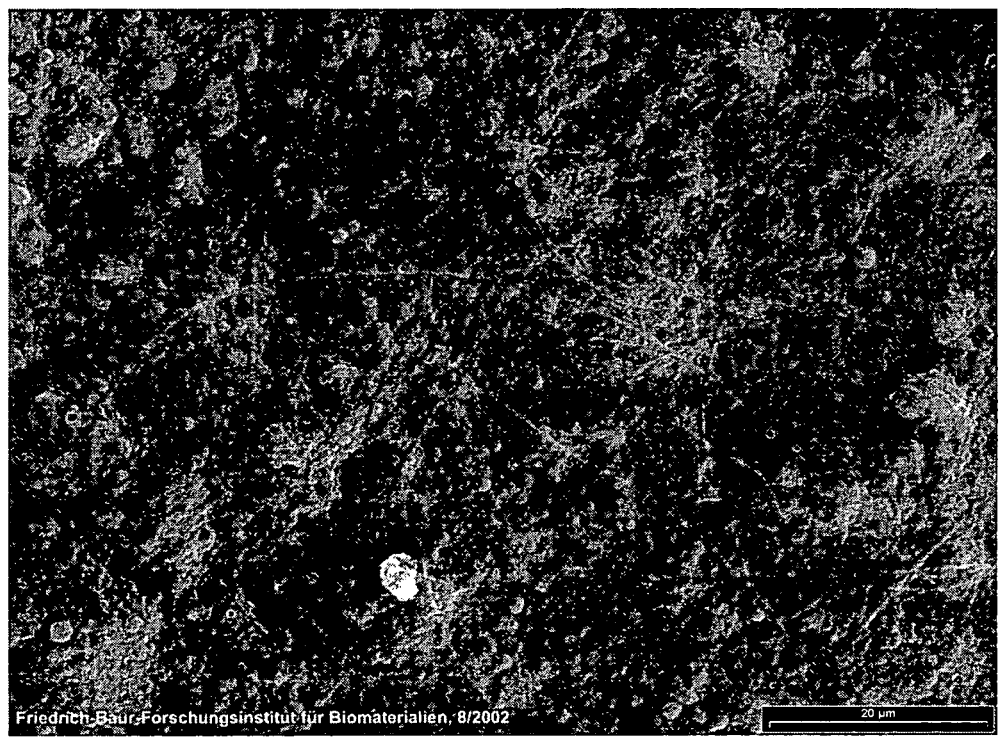
FIG. 1 is a SEM (scanning electron microscope) photograph illustrating the surface of a dry equine collagen foil. Collagen fibrils are clearly illustrated. Substantial non-porosity of the surface is evident from the picture.
Figure 2A:
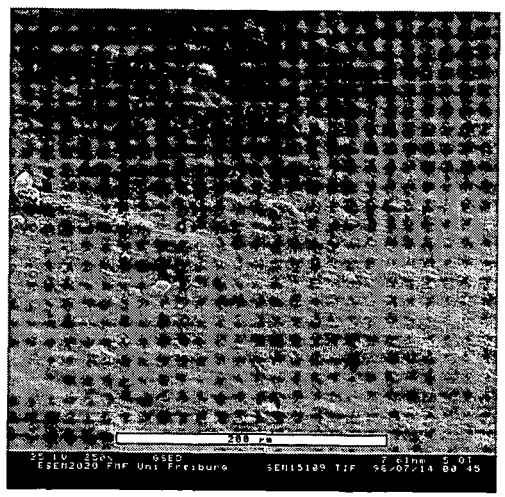
FIGS. 2A and 2B are photographs taken under ESEM (environmental scanning electron microscopy) conditions, which means near natural conditions in a slightly humid atmosphere, illustrating the upper surface, seen from the side of an equine collagen foil. Substantial non-porosity is evident from the photographs.
Figure 2B:
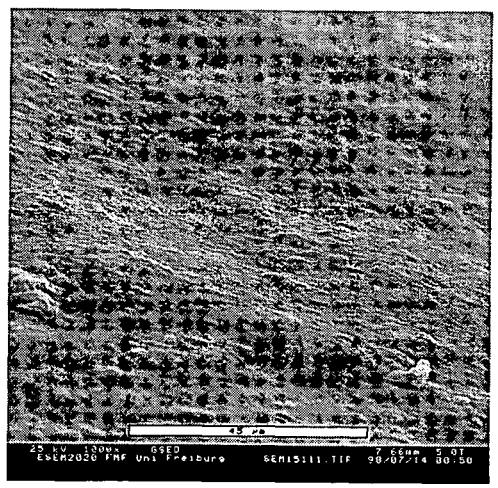
Figure 3A:
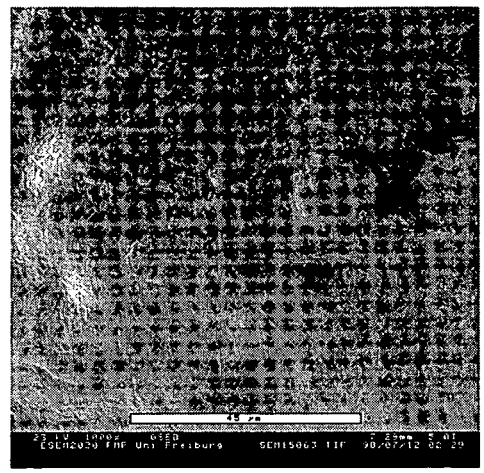
FIGS. 3A and 3B are photographs taken under ESEM conditions illustrating the lower surface of an equine collagen foil. Collagen fibrils are illustrated in FIG. 3A. Substantial non-porosity of the surface is evident from the pictures.
Figure 3B:
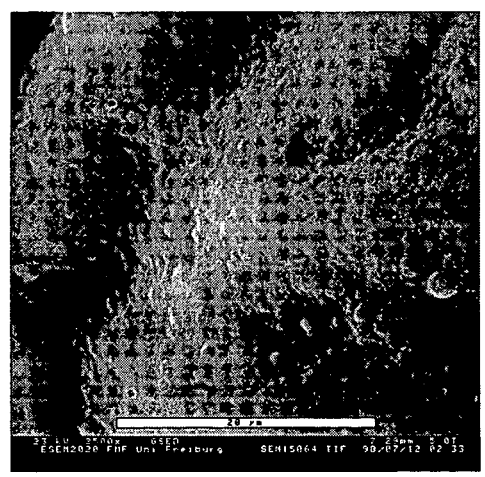

The equine collagen foil utilized in one embodiment of the present invention is a non-naturally occurring multi-layered collagen membrane consisting of numerous multi-directional intertwined collagen fibrils. An illustration of a dry equine collagen foil may be seen in FIG. 1. The photomicrograph (SEM) illustrates the surface of the equine collagen foil in which collagen fibrils are embedded. A photograph may be seen in FIGS. 2A-2B of the upper surface of the equine collagen foil under ESEM (Environmental Scanning Electron Microscopy) conditions, in which a slightly humid atmosphere provides near natural conditions. The collagen fibrils are visible on the surface. The surface appears smooth and substantially non-porous. Photographs (ESEM) of the lower surface of equine collagen foil are provided in FIGS. 3A and 3B. The lower surface photograph also illustrates the substantial non-porosity of the equine collagen foil.

Figure 4:
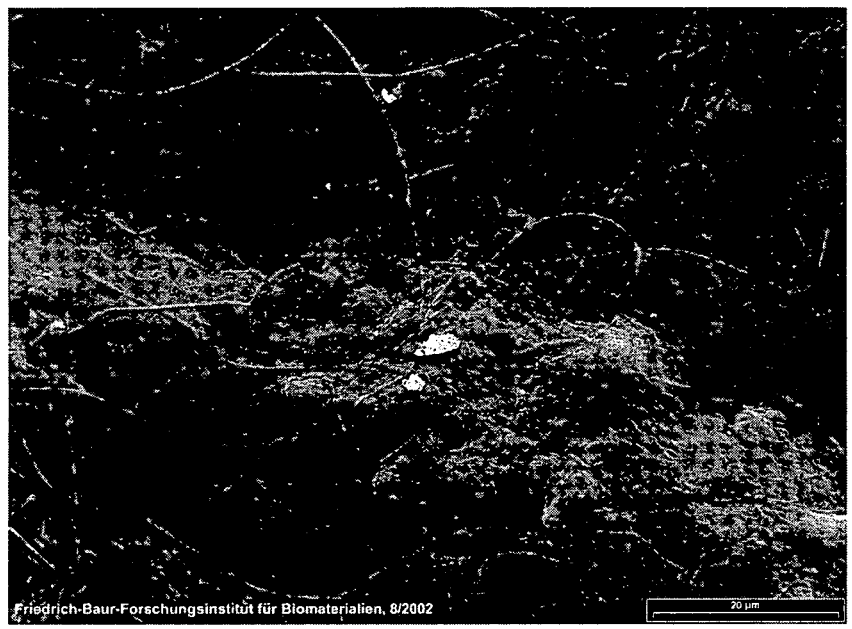
FIG. 4 is a SEM photograph illustrating the surface of a hydrated equine collagen foil. Collagen fibrils are clearly illustrated in FIG. 4. Substantial non-porosity of the surface is evident from the picture.

Prior to using the equine collagen foil to repair dura mater tissue of a mammal, the dry equine collagen foil material may be hydrated. FIG. 4 is a SEM photograph illustrating the surface of a hydrated equine collagen foil wherein collagen fibrils are clearly shown. Substantial non-porosity of the surface is evident from the picture.

The unique orientation of the collagen fibres in two-dimensional directions in the multiple layers is primarily responsible for the liquid-tightness even under high hydrostatic pressure and provides great strength with high elasticity. Due to the numerous parallel-oriented thin collagen fibril layers of the equine collagen foil, this material is suitable for temporarily replacing the body's own dura mater in covering the defect after implantation to achieve a liquid-tight cerebrospinal fluid-leakage closure and provides a biomatrix scaffold for cell ingrowth for forming a neodura. This property is important in the wound healing process as it reduces the risk of the patient developing the condition of liquorrhea.

Equine Collagen Foil Structure and Resorption Characteristics

The equine collagen foil is resorbable by the mammal in which it is implanted. It is believed that this property is enhanced by the structure of the equine collagen foil. The process utilized to produce the equine collagen foil forms stacked layers of collagen fibrils. Between each layer are interstices into which cells and vasculature of the patient can migrate and form neodura tissue.

Each layer of collagen fibrils is substantially non-porous. The few pores which may be present are typically isolated from one another and do not interconnect through multiple layers of collagen fibrils. The multiple layer structure of the present invention enhances the liquid-tight characteristic of the equine collagen foil. Scanning electron microscope pictures of FIGS. 1 to 4 illustrate the non-porous nature of the equine collagen foil.

Figure 5A:
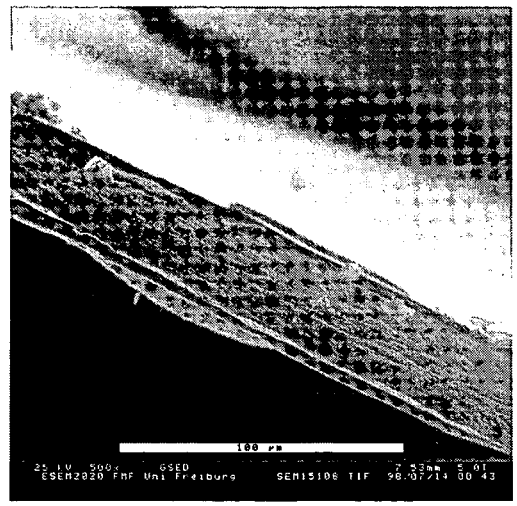
FIGS. 5A, 5B, and 5C are photographs taken under ESEM conditions (humid atmosphere) illustrating the cross section of an equine collagen foil. The material reveals a structure like a stack of sheets packed very tightly together. Interstices between the collagen layers are shown in the picture.
Figure 5B:
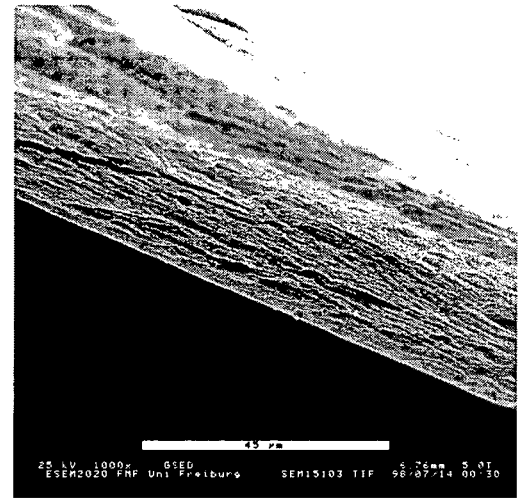
Figure 5C:
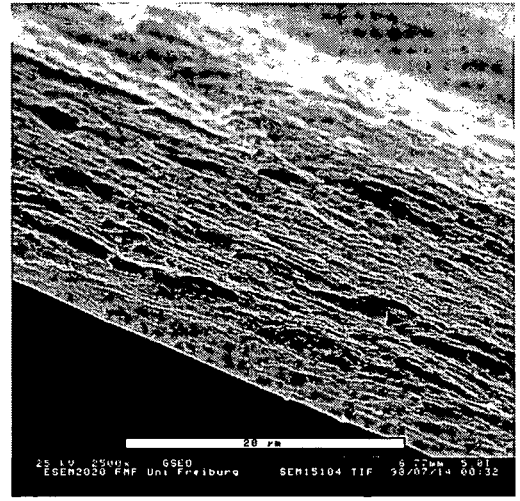
Figure 6A:
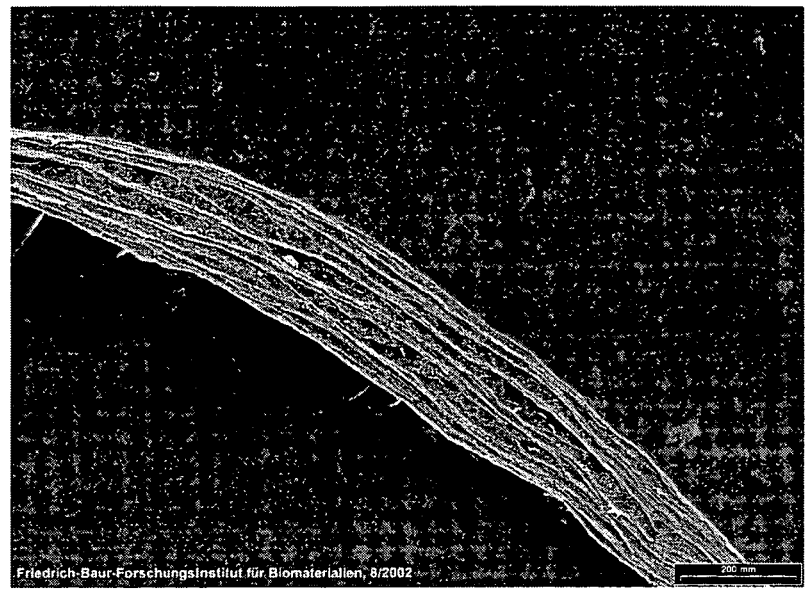
FIGS. 6A and 6B are SEM photographs illustrating the cross section of a dry equine collagen foil. Multiple layers of collagen and interstices between the collagen layers are illustrated in the pictures.
Figure 6B:
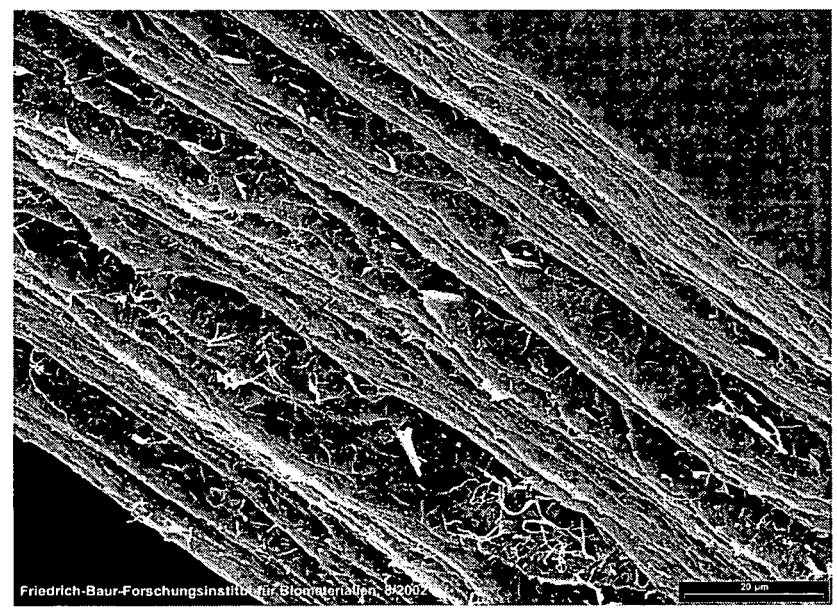

While the equine collagen foil is substantially non-porous, interstices exist between the layers of collagen fibrils. The interstices and layered characteristics may be readily observed in FIGS. 5A, 5B, and 5C which are cross-sectional photographs of the equine collagen foil under ESEM conditions (humid atmosphere). FIGS. 6A and 6B are SEM photographs of the dry equine collagen foil. Thus, the equine collagen foil is analogous to a stack of pages wherein each page is substantially smooth and non-porous, with a space between each page. When in its dry form (FIGS. 6A and 6B), the interstices are more pronounced. The interstices become reduced when the equine collagen foil is observed under near natural conditions in a slightly humid atmosphere. FIGS. 5A, 5B and 5C are pictures of cross sections of equine collagen foil in a humid atmosphere, wherein the reduction of the interstices of the equine collagen foil is illustrated.

In addition to promoting a liquid-tight property, the numerous parallel-oriented thin collagen fibril layers of the equine collagen foil simultaneously serve as a biomatrix scaffold for cell ingrowth for de novo construction of the body's own dura. Previously, it was commonly believed that a porous scaffold structure was necessary to promote the ingrowth of autonomic tissue and vasculature into a replacement dura mater tissue. It has been surprisingly discovered that the non-porous, layered structure of the equine collagen foil promotes the ingrowth of cells, vasculature, and the formation of new collagen structures across the equine collagen foil and in the interstices that exist between its multiple layers, forming a neodura with a typical layer structure of a natural dura within weeks of implantation. As described further below and in Example 1, the ingrowth of cells, vasculature, and new collagen structure is so extensive that within weeks post-operation, the neodura becomes difficult to distinguish from a patient's previously existing dura mater tissue. At approximately four to eight weeks post operation, the cellular organization of meningeal cells is about 40% to 70%. After about sixteen weeks, the graft is fully organized (100%).

Animal experiments demonstrate quick cellular infiltration in the area of the multi-layered equine collagen foil. Histologically, dense infiltration of the collagen biomatrix with lymphocytes, macrophages and fibroblasts was observed within 14 days after implantation. Capillaries form in the graft later in time. A continuous transition between the equine collagen foil and surrounding dura due to the neogenesis of collagen fibres is readily evident. After only 4 weeks, the equine collagen foil is partially replaced by the body's own loosely structured tissue. After 24 weeks, it is difficult to distinguish the patient's previously existing dura from the newly-formed neo-dura-like connective tissue architecture replacing the implanted equine collagen foil in the defect area.

Disease Transmission/Immune Response

A significant benefit of using the equine collagen foil of the present invention is the substantially low risk of transmitting a disease to a patient in which it is implanted. The manufacturing process in which the collagen fibrils are treated with acids (e.g., hydrochloric acid, acetic acid, and the like) and bases, such as sodium hydroxide, to produce the equine collagen foil beneficially acts to inactivate or reduce the infectious levels of bacteria, viruses, and prions that may be present. Treatment of biomaterial with hydrochloric acid, sodium hydroxide, ethylene oxide (ETO), and the like have been recognized by governmental agencies as approved methods within drug and biomaterial regulations to inactivate prions and viruses. Such treatment may, under some regulations, reduce the regulatory requirements for testing the equine collagen foil on a batch-by-batch basis. Thus, the treatment of the collagen fibrils during the manufacturing process enhances the product safety and reduces the risk of disease transmission to a patient.

Equine material that has been subjected to the manufacturing process described above is not known to transmit any pathogens to patients. Thus, in addition to the manufacturing process, utilization of equine-based collagen further avoids the risks of transmitting spongiform encephalitis that have been previously associated with human cadaveric substitutes. Use of collagen derived from an equine origin, such as collagen derived from equine Achilles tendons avoids the risks of transmitting transmissible spongiform encephalopathy (TSE), which is also known as bovine spongiform encephalopathy (BSE) or scrapie. Transmission of this disease has been associated with the use of biological material obtained from ruminant sources (e.g., biological material from cattle, goats, sheep, and the like).

The equine collagen foil of the present invention wherein the collagen is derived from an equine origin and treated (e.g., with enzymes) additionally reduces the risk of eliciting an immune response. No immune responses have been reported for a period of over ten years during which equine-based collagen has been used in tissue replacement procedures (for tissues other than dura mater).

The equine-derived collagen foil also results in a reduced inflammatory response. When compared to dura mater substitutes that contain collagen derived from sources such as human fascia lata, the number of inflammatory cells resulting from the implantation of the replacement equine collagen foil is significantly lower. The inflammatory processes elicited by the implantation of equine collagen foil are also much shorter in duration compared to replacement dura mater devices derived from other sources. These properties significantly reduce the risk of graft rejection of the equine collagen foil by a patient's immune system, thereby improving the success of neurosurgical procedures requiring dura mater replacement.

Volume/Size Stability

Problems can arise if a replacement dura mater significantly expands or contracts when hydrated. Porous collagen dura mater replacement products of the prior art have in some instances tended to shrink significantly after hydration. In such instances, the replacement dura mater may tug at sutures that attach it to the dura mater of the patient causing damage to the implant and to the autologous dura mater and surgical site. Other complications include pressure exerted at the surgical site if the replacement dura mater continues to expand after it is implanted, exerting undesired pressure on adjacent neurological tissue.

The change in volume of the equine collagen foil of the present invention is small or negligible when hydrated. In contrast to porous replacement products, the equine collagen foil substantially retains its size and shape upon being hydrated, having excellent shape stability, remaining biostable even after hydration, and causing no problems of swelling or shrinking in the brain following implantation. Once hydrated and implanted, equine collagen foil does not significantly expand or contract in area or thickness to the extent that it would tear surgical sutures or break apart fibrin glue seals that hold the equine collagen foil to the patient's dura mater.

In one embodiment, the shrinking or swelling of the area of the dry equine collagen foil may vary from about −5% to about 20% when completely hydrated. In another embodiment, the area of the dry equine collagen foil may vary between about −5% to about 10% when completely hydrated. In another embodiment, the area of the dry equine collagen foil varies between about −5% to about 5% percent when completely hydrated. In another embodiment, the area of the dry equine collagen foil increases no more than about 4 percent when completely hydrated.

In one embodiment, the equine collagen foil increases up to about 4 times its dry thickness when it is completely hydrated. In another embodiment, the equine collagen foil increases up to about 3 times its dry thickness when it is completely hydrated. In another embodiment, the equine collagen foil increases to about twice its dry thickness when it is completely hydrated.

The thickness of the adult human dura varies from approximately 0.5 mm at the skull base to approximately 2.0 mm. The thickness of the dura mater may also vary depending on the age of the patient wherein infants and young children would typically be expected to have thinner dura mater tissue than adults. The thickness of the equine collagen foil of the present invention may be formulated to vary for the desired area of application and the treated patient.

In one embodiment, the equine collagen foil of the present invention, when in its dry form, has a thickness between about 0.01 mm to about 3.0 mm. In another embodiment, the equine collagen foil has a thickness between about 0.02 mm to about 2.0 mm. In another embodiment, the equine collagen foil has a thickness between about 0.03 mm to about 1.5 mm. In another embodiment, the equine collagen foil has a thickness between about 0.05 mm to about 1 mm. In still another embodiment, the equine collagen foil has a thickness of about 1.0 mm or less.

The dry weight of the equine collagen foil is dependent on its desired thickness. In one embodiment, the dry weight of the equine collagen foil is between about 1 $mg/cm^2$ to about 50 $mg/cm^2$. In another embodiment, the dry weight of the equine collagen foil is between about 1.5 $mg/cm^2$ to about 30 $mg/cm^2$. In another embodiment, the dry weight of the equine collagen foil is between about 2 $mg/cm^2$ to about 20 $mg/cm^2$. In another embodiment, the dry weight of the equine collagen foil is between about 2.5 $mg/cm^2$ to about 15 $mg/cm^2$. In another embodiment, the dry weight of the equine collagen foil is between about 3 $mg/cm^2$ to about 10 $mg/cm^2$.

In one embodiment, the weight of the equine collagen foil increases up to about 15 times its dry weight upon hydration. In another embodiment, the weight of the equine collagen foil increases up to about 10 times its dry weight upon hydration. In another embodiment, the weight of the equine collagen foil increases up to about 7 times its dry weight upon hydration. In still another embodiment, the weight of the equine collagen foil increases up to about 5 times upon hydration from its dry state.

To serve as adequate dura mater replacements, implanted dura substitutes should not become flabby but instead possess a rather high stability/tensile strength even when hydrated. The equine collagen foil of the present invention beneficially has high tensile strength, which improves and supports the handling of the equine collagen foil during its surgical application and provides an increased mechanical stability after its implantation. Comparative experiments are outlined in the examples below wherein the tensile strength of the equine collagen foil was superior compared to porous collagen preparations (e.g., collagen foams). Additionally, increasing the thickness of the equine collagen foil can significantly increase the tensile strength.

The propensity of equine collagen foil material to tear under exerted pressure may be measured as its "ultimate tensile load" or "ultimate tensile force," hereinafter referred to as "ultimate tensile force." The ultimate tensile force of an equine collagen foil may be determined by subjecting pressure to a strip of equine collagen foil having a specified width and determining the amount of pressure applied that results in failure (e.g., tearing or rupturing) of the equine collagen foil. Ultimate tensile force may be quantified using the following equation:

"Ultimate Tensile Force"=force applied/width of equine collagen foil strip=Newtons/cm-strip.

In one embodiment, the equine collagen foil has an ultimate tensile force between about 1 and about 30 Newtons/cm-strip, preferably between about 1.5 and about 15 Newtons/cm-strip, preferably between about 2 and about 10 Newtons/cm-strip, still more preferably, between about 3 and about 6 Newtons/cm-strip.

While the equine collagen foil of the present invention has a high tensile strength, it remains elastic and flexible when hydrated. This feature permits the equine collagen foil to optimally adapt to the anatomic conditions (e.g., curves) present at the implantation site.

When in its hydrated state, the equine collagen foil can be easily moved around in the surgical site and optimally modelled to the shape of the defect where it is being implanted. Once implanted, the equine collagen foil graft remains smooth and mobile. Over time, cells and vasculature migrate across the equine collagen foil, eventually replacing it with a dura-like neodura. After cellular organization with meningeal cells, the equine collagen foil does not adhere to the neural, brain, skull, or spinal column tissue.

Preparation of Equine Collagen Foil

The equine collagen foil of the present invention can be produced from suspensions of high molecular weight collagen fibrils through a controlled drying process. A graded precipitation of the collagen fibril suspension results from the evaporation of water and simultaneous pH elevation. The controlled drying process results in a multi-layered construction of a collagen foil that can be implanted by neurosurgeons as a substitute for human dura mater. The multi-layered collagen foil construction provides a number of the above-described properties that are beneficial in a dura mater substitute and as a biomatrix for the regeneration of living dura tissue.

In one embodiment, the process to produce the equine collagen foil of the present invention removes all cellular components producing a equine collagen foil of collagen fibrils that consists essentially of acellular components.

Using established procedures in collagen chemistry, collagen-containing tissue is used as a starting material for the preparation of the equine collagen foil of the present invention. In one embodiment, equine tendons are used as a starting material. In a further embodiment, equine Achilles tendons are used as a starting material.

In one embodiment, the starting material, for example equine Achilles tendons, is first ground and treated for at least one hour with 1 N sodium hydroxide and neutralized with hydrochloric acid. The collagen starting material is treated in acid conditions at pH 2. The acid utilized may be hydrochloric acid, acetic acid, or the like. Subsequently, the non-collagenous proteins and intermolecular cross-linking bonds present in the starting material are degraded enzymatically with pepsin to form a suspension of collagen.

The suspension is then neutralized. In one embodiment, the suspension is neutralized to between about pH 6.5 to about pH 8.0. In another embodiment, the suspension is neutralized to between about pH 6.9 to about pH 7.5. In another embodiment, the suspension is neutralized to about pH 7.

The collagen suspension is centrifuged, the supernatant removed, and the precipitate resuspended in acetic acid at about pH 2-4.5. Non-collagenous proteins are thereby successfully removed from the suspension of collagen.

Repetition of the above-described steps may be conducted as necessary to remove residual non-collagenous proteins present in the precipitate.

A surprising result of the production process of the equine collagen foil is that a controlled pH elevation of the collagen suspension in acetic acid is achieved due to the specified removal of water by evaporation over a long period of time, e.g., 24 hours. The specified elevation of pH causes the precipitation of the multi-directional intertwined collagen fibrils in two-dimensional direction layers forming a multi-layered construction of the equine collagen foil. In one embodiment, the process is performed in a drying oven at a temperature of about 20° C. to about 55° C., with equipment to remove steam and the simultaneous steam neutralization of acetic acid. In another embodiment, the process is performed in a drying oven at a temperature of about 30° C. to about 45° C.

The equine collagen foil that results from the production process is considered to be in its dry form when further loss of water is not detected or is negligible. The water content of the "dry form" of equine collagen foil is typically between about 2% to about 18% by weight. The relatively high residual water content present in the "dry form" of the equine collagen foil prevents or restrains the denaturation of collagen molecules that comprise the equine collagen foil.

The above-described process is responsible for the precipitation of the collagen fibrils from the suspension since components with low solubility fall out at the beginning of the process at a low pH elevation. This technique results in a precipitation of collagen fibrils during water evaporation and simultaneous pH elevation.

During the precipitation process, the collagen fibrils become naturally cross-linked as the fibrils precipitate out of solution to form a collagen foil. Unlike cross-linking the collagen fibrils with chemicals or radiation (e.g., ionizing or ultraviolet radiation), which can result in increased resorption times, allowing natural cross-linking of the collagen fibrils promotes reduced resorption times once the equine collagen foil is implanted. The natural cross-linking of the fibrils in the collagen foil utilized in the invention occurs by natural, physiological-like means. Primarily this natural cross-linking is through non-covalent interactions (e.g., van der Waals or dipole-dipole interactions) or by the formation of readily dissociable Schiff base bonds between the amino acid side chains of the collagen molecule. Intermolecular crosslinking of collagen is responsible for physical and chemical stability. The key step in the formation of collagen cross-links depends on the enzymatic conversion of lysine or hydroxylysine residues and gives rise to aldehydes, allysine and hydroxyallysine. These aldehyde groups spontaneously react with reactive amino groups resulting in the formation of Schiff-base components containing labile aldolcondensation products with labile aldimine links (—CH=N—) Thus, the fibrils of the product of the present invention may be dissociated by treatment with, for example, a weak acid. Cross-linking arising from the use of chemical cross-linking agents can be detected from the presence of stable covalently cross-linked cross-linking moieties. Commonly, this is accomplished by using a Schiff-base reagent (e.g., glutaraldehyde) to form Schiff base reaction products, and then stabilizing the bonds through either an Amadori rearrangement or reducing conditions. In addition collagen can be cross-linked by various bifunctional carbodiimide reagents. Cross-linking arising from the use of radiation can be detected by the presence of stable covalent bonds between the collagen fibrils, caused by the reaction of free radical moieties generated during irradiation. The fibrils in the product of the present invention, on the other hand, are substantially uncross-linked with any stable covalent bonds, and have not been treated in a chemical or irradiative manner. Thus, any association between the fibrils in the product of the invention is substantially non-covalent or readily reversible, and are not stably cross-linked. Chemicals such as cyanamide, glutaraldehyde, formaldehyde, acrylamide, carbodiimidediones, diimidates, bisacrylamides, and the like have been utilized in the past to chemically cross-link collagen fibrils in dura mater substitutes. Use of such chemicals, however, may result in toxicity risks associated with inadvertently contacting brain tissue with residual chemicals in a dura mater substitute. The precipitation process thereby avoids the toxicity risks of cross-linking chemicals and longer resorption times associated with cross-linking the collagen fibrils with chemicals or radiation.

The resulting dried, precipitated, collagen composition forms an equine collagen foil comprised of a high-molecular weight multi-layered collagen membrane consisting of numerous multi-directional naturally intertwined collagen fibrils. The equine collagen foil primarily contains interstitial Type I collagen. The equine collagen foil has substantially no pores and is primarily liquid-tight. Immune diffusion tests may be conducted on the product to guarantee the absence of foreign protein.

The above-described process used to produce the equine collagen foil for use in the present invention is also utilized by Resorba Wundversorgung GmbH & Co. KG, Nuremberg, Germany, in manufacturing collagen foils commercially available from Baxter AG, Vienna, Austria. The commercially available foils are indicated for use as haemostatic agents, as temporary tissue substitutes, for the covering of wounds, and as fibrin sealant carrier substances.

The thickness of the equine collagen foil for use in the present invention may vary as required by a particular application. For example, in repairing paediatric dura mater tissue, a thinner equine collagen foil may be utilized, whereas a thicker equine collagen foil may be utilized in repairing adult dura mater tissue.

The thickness of the equine collagen foil can be controlled by varying the amount of starting material utilized to produce a particular size of equine collagen foil.

The equine collagen foil is gas-sterilized with ethylene oxide (ETO) or similar sterilization gas or by irradiation.

Attachment Procedures

Prior to use, the dry equine collagen foil may be hydrated, e.g., in physiological saline. In one embodiment, the physiological saline comprises a 0.9% sodium chloride solution. In another embodiment, the equine collagen foil is hydrated in excipients or drug-containing solutions. The length of time necessary to hydrate the equine collagen foil is related to the thickness of the foil. The equine collagen foil is hydrated until it is consistent in thickness across its entire area. In one embodiment the equine collagen foil is hydrated between about 5 seconds and about 1 hour in physiological saline. In another embodiment, the equine collagen foil is hydrated between about 5 seconds and about 30 minutes in physiological saline. In another embodiment, the equine collagen foil is hydrated between about 5 seconds and about 20 minutes in physiological saline. In another embodiment, the equine collagen foil is hydrated between about 5 seconds and about 10 minutes in physiological saline. In still another embodiment, the equine collagen foil is hydrated between about 1 minute and about 6 minutes in physiological saline. In another embodiment, the equine collagen foil is hydrated about 5 minutes in physiological saline. In another embodiment, the equine collagen foil is not hydrated prior to implantation.

The equine collagen foil may be attached to the patient's dura mater by established surgical techniques, e.g., by fibrin sealant, tissue glue, surgical sutures, or by pressure fitting surgical techniques. Alternatively, the natural attraction between the equine collagen foil and dura mater tissue can be used to attach the equine collagen foil to the dura mater tissue without the use of any sealant, glue, sutures, or pressure fitting techniques. Once hydrated, the equine collagen foil can be cut slightly larger than the surgical opening in the patient's dura mater. The equine collagen foil thereby slightly overlaps the patient's dura mater to which it is attached. In one embodiment, the hydrated equine collagen foil is sized to have an approximately 0.5 cm to about 1 cm overlap with the dura. The amount of overlap can vary depending on the preferences and skill of the neurosurgeon.

In one embodiment, according to the well-known interaction of collagen with fibrin, the equine collagen foil can be attached to the dura mater with fibrin sealant approved for neurological use. Examples of fibrin sealant approved for neurological use include Tissucol and Tisseel fibrin sealants (Baxter AG, Vienna, Austria). Alternatively, a tissue glue that is approved for neurological use may also be utilized. The fibrin sealant or tissue glue may be applied in a continuous line around the portion of the equine collagen foil that overlaps the dura mater in order to form a liquid-tight seal. As described above, a liquid-tight seal is advantageous as it avoids complications associated with the loss of cerebrospinal fluid such as liquorrhea.

In another embodiment, the equine collagen foil produces a liquid-tight seal when attached to the autologous dura mater with a continuous line of fibrin sealant or tissue glue.

In another embodiment, the equine collagen foil that overlaps the dura mater can be dotted with fibrin sealant or tissue glue to attach it to the dura mater.

In another embodiment, the equine collagen foil is attached by surgically suturing it to the dura mater once it has been positioned to the desired implantation site. While this embodiment may be utilized to attach the equine collagen foil to the autologous dura mater of the patient, the sutures may cause branch canals, which in turn may result in fistulas and leakage of cerebrospinal fluid. If the equine collagen foil is to be sutured, tensionless suturing techniques must be used to prevent tearing the foil. It is recommended to seal suture lines, for example, with a fibrin sealant.

In another embodiment, the equine collagen foil is positioned and implanted according to pressure fitting techniques known in the art. In this technique, the equine collagen foil is positioned in the desired implantation site and held in place by the natural internal pressure present in the cranium or spinal column. Thus, the graft remains in place without the use of surgical sutures, fibrin sealant, or tissue glue.

In another embodiment, the equine collagen foil is positioned and implanted without the use of any sealant, glue, sutures, or pressure fitting techniques. In this technique, the equine collagen foil is positioned in the desired implantation site and held in place by the natural attraction or adhesion that occurs between the equine collagen foil and the dura mater tissue.

The equine collagen foil of the present invention can be utilized as a replacement dura mater graft to repair human dura mater tissue due to a congenital condition, birth defect, disease, injury, tumor removal or other surgical procedure that disrupts or penetrates the dura mater of a patient, or any other condition in which the dura mater requires repair. The equine collagen foil may also be utilized to repair dura mater tissue of other mammals, including, but not limited to sheep, monkeys, horses, laboratory animals, or other mammals. The equine collagen foil can be used to repair dura mater tissue in the cranium or along the spinal column.

The present invention is further directed to a kit comprising equine collagen foil and instructions for its preparation and use as a replacement dura mater.

Contraindications

A patient known to have allergic reactions to horses or equine products would be contraindicated from receiving equine collagen foil.

Other contraindications could include patients that are to undergo radiation therapy shortly after surgery. For example, patients who are to receive radiation therapy shortly after a brain tumor resection are not good candidates for being recipients of the equine collagen foil of the present invention. The radiation therapy may slow or inhibit the growth of neodura, which is comprised of rapidly dividing cells, wherein the equine collagen foil is resorbed. In such a situation a non-resorbable replacement dura mater, such as Teflon, would be more suitable. A skilled surgeon, however, would recognize the treatments in which a non-resorbable replacement would be necessary.

DEFINITIONS

"Equine collagen foil" means a biomatrix (i.e. a matrix of biocompatible material) of equine collagen fibrils treated to remove cellular components and to form a sheet of collagen fibrils. The term "equine collagen foil" does not include a composite foil of one or more substantially non-porous sheets of collagen fibrils bonded to one or more porous sheets of collagen.

"Dura mater tissue" means the autologous dura mater tissue of a mammal.

"Non-naturally occurring biomatrix" means a manufactured matrix or framework comprising collagen fibrils formed from (1) a material existing in nature (i.e., natural material) that has been treated or processed in a manner in which the collagen fibrils contained in the natural material have been moved or repositioned from their naturally-occurring arrangement within the collagen structure of the natural material; or (2) a material not existing in nature (i.e., a non-natural material) treated or processed with collagen fibrils. For example, a non-naturally occurring biomatrix may be formed from starting material comprising collagen that has been mechanically or chemically processed (e.g., ground, chopped, etc.). In contrast, a collagen biomatrix that is formed from the treatment or processing of starting material in a manner which preserves the structure of the collagen framework is not a non-naturally occurring biomatrix (e.g., epidermal tissue treated to remove cellular components while preserving the naturally occurring collagen structure).

"Substantially non-porous" means that any pores that are present in an equine collagen foil as a result of precipitation of collagen fibrils to form a collagen sheet are primarily isolated from one another. Pores which may be connected to each other are not interconnected in a manner which traverses the thickness of the equine collagen foil. Mechanical perforations that create holes in the equine collagen foil are not pores. Preferably, the material appears to be substantially free of pores that would be visible using a scanning electron microscope at 1500× magnification.

The following examples will further illustrate the invention.

Example 1

This example presents the results of experiments in sheep to evaluate an equine collagen foil for its suitability as a dura mater substitute used to repair dura mater tissue and as a biomatrix for dura regeneration.

An experiment was conducted to assess the properties of an equine collagen foil for use as cranial dura mater substitute as investigated in a sheep model. The equine collagen foil comprises native equine collagen fibrils (5.6 mg/cm$^2$) purified from minced equine Achilles tendon and contains no cellular components.

The reference product used was preserved human cadaveric dura (Tutoplast® Dura). Both products were attached in position using fibrin glue only (Tissucol Duo S Immuno, Baxter AG, Vienna, Austria).

The following items were studied:
Macroscopic aspects of incorporation of the two grafts;
Reactions of adjacent tissue structures (inflammation, adhesion, fibrosis, necrosis); and
Histological assessment of the incorporation process and connective tissue organization The purification process for producing equine collagen foil begins with at least one hour of sodium hydroxide solution treatment of the tendon starting material, followed by neutralization in hydrochloric acid. Pepsin is then used to break down the tendons. The colloidal collagen thus produced is precipitated as fibrils. Drying and gas sterilization then yields equine collagen foil with 5.6 mg of native collagen fibrils per square centimeter. Nothing else is added and no artifical methods for cross linkage (i.e. involving chemicals or radiation) are performed. Immunodiffusion tests ensure that no foreign proteins are present.

Material and Methods
Experimental Animals

The study was performed in 25 adult sheep. The sheep were mixed-breed domestic animals used in agriculture. The animals weighed on average 53.0 kg at the time of surgery and their average age was 2 years. All the animals were female. The animals were kept in the animal pen of Luebeck Medical University which is equipped with roofed structures and an open-air enclosure. The animals were given conventional mixed feed. The animals were divided in groups of five for histology tests and characterization of diverse stages of graft incorporation (Group 1-Group 5). Survival times per group were 2, 4, 8, 16, and 24 weeks.

Study Product

The investigational equine collagen foil is made of native equine collagen fibrils (mainly interstitial type I collagen). One square centimeter of the material contains 5.6 milligrams of collagen fibrils with no cellular components. The comparator (Tutoplast® Dura, Tutogen Medical GmbH, Neunkirchen a. Brand, Germany) is a human cadaveric dura preserved by a tissue-sparing process.

Fibrin glue, Tissucol Duo S, was used to attach the grafts to the dura mater. This biological dual-component glue consists of a pre-filled syringe containing human plasma proteins, fibrinogen, clotting factor XIII, plasma fibronectin and aprotinin, and another pre-filled syringe containing thrombin and calcium chloride.

Anaesthesia

The animals were premedicated with an intramuscular injection of xylazine hydrochloride, (Rompun 2%, Bayer AG, Leverkusen, Germany), dosage: 0.1 mg per kg body weight, (S)-ketamine (Ketanest S, Parke-Davis GmbH, Karlsruhe, Germany) dosage: 2 mg per kg body weight, and 0.5 mg atropine, 1 ml injection solution, (Atropinsulfat Braun 0.5 mg, B. Braun Melsungen AG, Melsungen, Germany), in an injection cocktail. A venous and arterial fine was inserted in the right ear. Propofol (Disoprivan 2%, AstraZeneca GmbH, Wedel, Germany) 1 mg/kg body weight was administered for anaesthesia. The animals were intubated endotracheally (I.D. 7.0 mm) and 100% oxygen was administered for controlled normoventilation (Sulla 808V anaesthesia ventilator, Dräger, Luebeck, Germany).

Propofol, (S)-ketamine, and sevoflurane were administered to maintain balanced anaesthesia. Pressure and volume ratios within the respiratory cycle, inspiratory oxygen fraction (Oxydig, Dräger, Luebeck, Germany), end-expiratory carbohydrate concentration (Kapnodig, Dräger, Luebeck, Germany), electrocardiogram and invasive arterial blood pressure were monitored during surgery.

Preoperative Antibiotic Prophylaxis

Immediately before surgery, each animal received an intravenous dose of 2.0 g cefazolin (Basocef 2.0 g, Curasan AG, Kleinostheim, Germany). Antibiotic prophylaxis was maintained for another 4 days postoperatively by two subcutaneous doses of a depot product, Strepdipen-Suspension (1.0 ml contains 100 000 IU benzylpenicillin benzathine and 100 000 IU dihydrostreptomycin sulphate; dosage 1.0 ml per kg body weight). The subcutaneous injections were administered immediately on completion of the procedure and again 48 hours later.

Surgical Technique

The already intubated animal was placed in a left lateral position. The head was then turned to the right and held in a horizontal position by clamping to the operating table. The skull was then shaved thoroughly, the skin was degreased with petrol and then disinfected. A sterile sheet with an opening exposing the area to be operated on was affixed and the entire animal was covered with sterile covers.

The first skin incision was made 1.5 cm to the left of the midline and extended for approximately 6 cm. Any bleeding from the scalp was coagulated using bipolar forceps. A retractor was applied and the skull bone was exposed in the temporoparietal region by retracting and spreading the galea aponeurotica. Two holes (0.8 cm in diameter) approximately 5 cm apart were then drilled using a manually operated drill. A saw (Mikrotom, Aesculap, Melsungen, Germany) was then used to remove a longitudinal oval disk of bone from the skull between the burr holes.

Any bleeding from the skull was stopped using bone wax. A scalpel was used to make an incision in the dura approximately 0.5 cm in length. Dura scissors were then used to cut an oval piece of dura mater measuring approximately 3×2 cm along the margin of the bone. Special care was taken not to injure the arachnoidea mater. A haemostyptic agent, TachoComb® (Nycomed Austria GmbH, Linz, Austria) was used to stop any bleeding from dural blood vessels.

Figure 7:
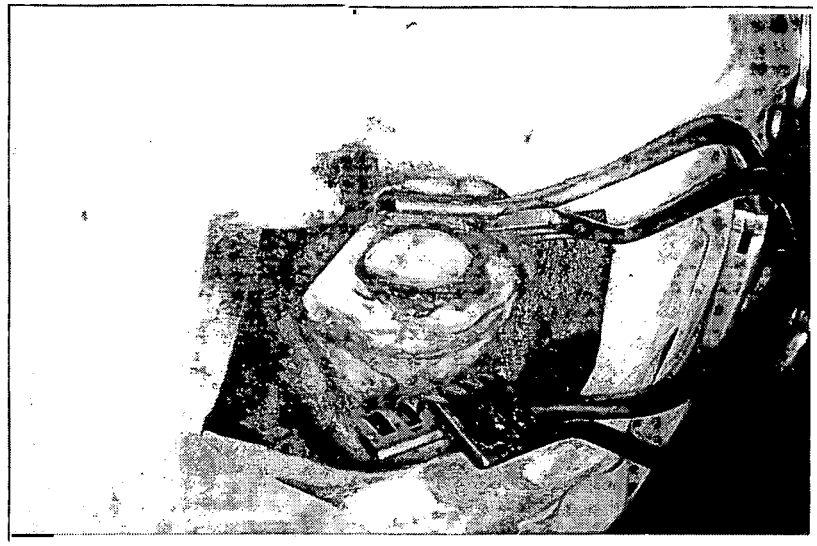
FIG. 7 is a photograph illustrating an intraoperative aspect of the left-sided dural defect after insertion of the equine collagen foil, the surrounding dural edges are covered with blood clots.

An oval piece of equine collagen foil (measuring 3.5×2.5 cm) was then cut to size and immersed for 5 minutes in sterile 0.9% saline. To close the defect, the equine collagen foil was tucked all round under the dura mater margins and dotted with fibrin glue to keep it in place. See FIG. 7.

The disc of skull was then reattached using two miniplates (Bioplates, Codman, Norderstedt, Germany). The galea was closed using absorbable suture (Vicryl 2.0) and the skin was sutured with Ethilon 3.0.

Figure 8:
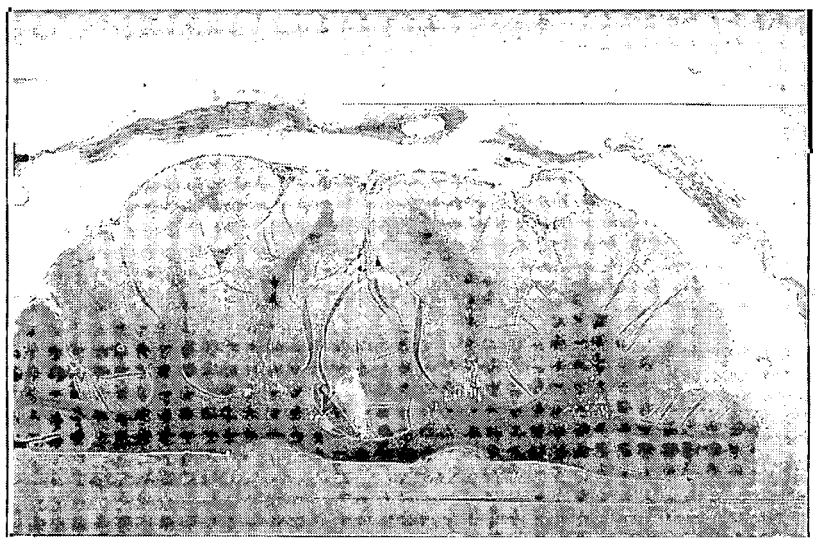
FIG. 8 is a photograph illustrating a Trichrom staining microscopic overview (frontal section) of the operation site showing cortical structures and the overlying dura mater with both grafts (equine collagen foil on the right side; Tutoplast® Dura on the left side) (8× magnification).

The Tutoplast® Dura product was applied in similar fashion on the right aspect of the skull. See FIG. 8. Both wounds were finally treated with a spray-on dressing (Hansaplast Spruhpflaster, Beiersdorf AG, Hamburg, Germany).

The average operating time was 120 minutes. The mean period from induction of anaesthesia to start of surgery was approximately 60 minutes and the mean time from end of suture until end of anaesthesia was 5 to 10 minutes.

Postoperative Observation of the Animals

The animals were returned to their pen approximately 30 minutes after extubation. They were checked at regular intervals by the surgeon, veterinarian and animal carers for signs of inflammation or neurological abnormalities. The animals were let into the open-air enclosure eight days after surgery.

Animal Euthanasia

The animals were killed for sampling purposes at the predefined survival times of 2, 4, 8, 16, and 24 weeks postoperatively.

Before the kill the animals were sedated by intramuscular injection of 1 mg per kg of body weight Rompun 2%. An electrocardiogram (ECG) monitor was hooked up and a venous and arterial line was placed in the right ear. The deeply sedated animals were then killed by intravenous injection of T-61® (Hoechst Roussel Vet, Somerville, N.J.); 1 ml injection solution contains 0.2 g embutramide, 0.05 g mebezonium iodide and 0.005 g tetracaine hydrochloride; dosage-0.3 ml per kg of body weight). The process was monitored by ECG and measurement of arterial pressure.

Sampling

The animals had their heads shaved and were positioned as described for the surgical procedure. A circular incision measuring approximately 9 cm in diameter was made in the skin around the two surgical scars. The galea aponeurotica was retracted to expose a large section of the skull cap and a hole was drilled in the right frontal region. A circular disk of skull measuring approximately 8 cm was removed with a saw. The entire graft site consisting of bone, dura and cerebral parenchyma was accessed by cutting along the margin of the bone with a scalpel. The dura and brain tissue were then carefully separated from the overlying bone and fixed in formalin for histological work-up. The graft sample measured approximately 7 cm in diameter.

Histological Methods

The graft samples were examined macroscopically and divided into frontal slices. The two surgical sites were prepared simultaneously. Five sections approximately 2-3 μm thick were taken from each sample.

Standard staining methods used to assess the changes included. Haematoxylin-Eosin for the cellular components, Elastica van Gieson for mesenchymal structures, Trichrome for mesenchymal structures and to assess collagen fibre neogenesis and an iron stain for determining the extent of bleeding.

Results

Intraoperative and Postoperative Course

Anaesthesia, surgery and the postoperative follow-up period were uneventful in all but two animals. One animal died during induction of anaesthesia as a result of refractory cardiac arrhythmia. Another animal died suddenly and unexpectedly 14 days after surgery following what was an uneventful postoperative course up to then. Microscopic examination of the brain showed extensive cortical necrosis with evidence of scarring. The most likely cause of death is therefore long-standing cerebral ischemia of unknown etiology.

There were very few intraoperative bleeds, which were mild and in most cases from small blood vessels of the dura mater. The bleeding was rapidly brought under control using bipolar forceps or haemostyptic agents.

None of the animals displayed neurological abnormalities during postoperative follow-up. Likewise, none of the animals displayed signs of inflammation, cerebrospinal fluid leakage or impaired wound healing.

Macroscopy

The following parameters were examined and quantified during removal of the samples from the surgical sites:
  Formation of adhesions between the skull and dura;
  Cerebrospinal fluid leakage and inflammatory changes;
  Visible changes to the dural grafts; and
  Meningocortical adhesions and cortical reaction.

Microscopy

The histology sections were evaluated systematically in terms of the following:
  Description and quantification of inflammatory reactions in the graft site (epidural, subdural, transitional zone between dura and graft);
  Degree of connective tissue organization of the graft;
  Extent of foreign body reaction;
  Changes to the subarachnoidal space (inflammatory processes, fibrosis vs. open subarachnoidal space); and
  Changes to the cortex (inflammation, necrosis).

Macroscopy and Histology Results

The histology results described below are identical in terms of cellular composition, while varying in intensity, in different frontal sections from the same animal and in all animals of the same group.

Macroscopic Assessment of Graft Incorporation

Removal of the skull after a period of 2 weeks discloses minimal adhesions bilaterally between the fibrin glue residues and the overlying bone. The adhesions are easily loosened. There are no signs of inflammation or seepage of cerebrospinal fluid in either dural graft site. Both grafts are spotted with individual blood clots measuring a few millimeters in diameter.

In the left hemisphere the equine collagen foil is still circumscribable as such and seems to be less transparent than its original ground-glass appearance. The collagen product retains its attachment to the dural margins when the dura is carefully lifted off the cortex. There are a few very slight adhesions which are very easily loosened without damaging the cortex.

The Tutoplast® Dura in the right hemisphere is unchanged to the naked eye. The Tutoplast® Dura becomes detached in places in the graft-dural contact zone when the product is removed. There are a few subarachnoidal adhesions when the dura is lifted off the cortex, but they are easily loosened with forceps.

Four weeks postoperatively, there are still a few adhesions between the margins of the overlying bone and the dura below; these are due to fibrin glue residues. The bone is easily loosened from the dura mater without tugging, causing no injury to the dura or graft. At the equine collagen foil site in the left hemisphere, the demarcation zone between the dura mater and graft is no longer clear. The graft is less transparent than before and has taken on a pale red colour. The aspect of the graft facing the brain surface is homogenous, smooth and mobile. The subdural adhesions are no longer present. A few blood clot residues are visible.

The Tutoplast® Dura again looks unchanged to the naked eye. Inspection of the area of contact between the graft and dura discloses an inadequate, easily loosened attachment.

Figure 9:
FIG. 9 is a photograph illustrating dura mater grafts at eight weeks post-operation. On the left side, the Tutoplast® Dura cadaveric dura graft looks unchanged with clearly visible edges. Remaining parts of the thin connective tissue membrane covering the graft can be seen. On the right side, the equine collagen foil biomatrix graft looks fully incorporated into the surrounding dura. The dark spots are caused by small blood clot residues within the neodura.
Figure 10:
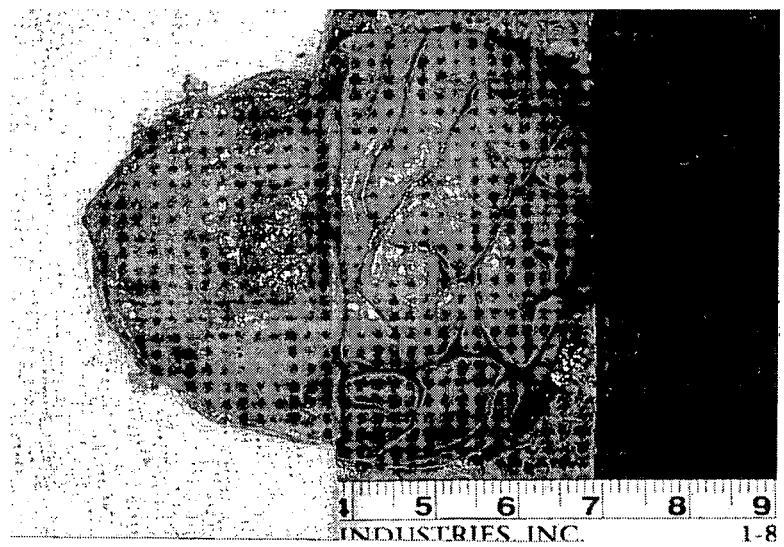
FIG. 10 is a photograph illustrating a macroscopic aspect of the equine collagen foil biomatrix graft facing the cortex, eight weeks post-operation. The graft appears smooth, mobile, and fully incorporated into the surrounding dura. No cortical lesions can be seen.
Figure 11:
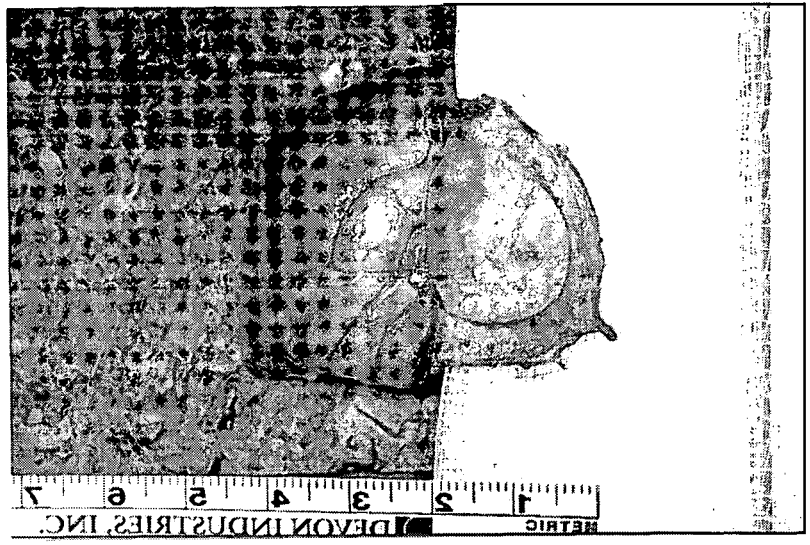
FIG. 11 is a photograph illustrating a macroscopic aspect of the Tutoplast® Dura cadaveric dura graft facing the cortex eight weeks post-operation. The graft looks smooth and homogeneous, but no signs of graft incorporation are present. Corticomeningeal adhesions are absent.

Eight weeks postoperatively, the zone of transition between the dura and the equine collagen foil graft in the left hemisphere is no longer present. Structural continuity is apparent on both sides of the meninx. The area where the equine collagen foil was placed is apparent only in a slightly thinner membrane and slightly reddish appearance. See FIGS. 9 and 10. The Tutoplast® Dura graft in the right hemisphere is at this time covered on both sides with a thin connective tissue membrane. See FIG. 11. The edges of the graft are still clearly visible below the overlapping dura. A slight tug on the Tutoplast® Dura is sufficient to detach it from the preformed dura.

After 16 weeks, neodura formation has proceeded further at the equine collagen foil site and the dura and neodura are barely distinguishable.

Connective tissue encapsulation of the Tutoplast® Dura graft in the right hemisphere has become more marked.

After a period of 24 weeks, sections of both grafting sites do not differ macroscopically from those of the previous group.

Microscopic Assessment of Graft Incorporation

Two weeks postoperatively, as expected, the equine collagen foil graft site discloses extensive areas of inflammatory change. The whole subarachnoidal space is closed by adhesions resulting from copious exudation from lymphocytes, segmented granulocytes and macrophages. Some areas of very extensive inflammatory exudation are also apparent above the graft. In addition to the lymphocytic and monocytic components, there are also small splinters of bone here with a corresponding foreign body reaction by polynuclear giant cells.

Figure 12:
FIG. 12 is a photograph illustrating two polynuclear giant cells with intracellular fragments of the equine collagen foil biomatrix graft, two weeks post-operation (hematoxillin-eosin (HE) staining; 800× magnification).

The equine collagen foil graft itself displays loosening of homogenous structures and invasion of inflammatory cells, heart-shaped or extensive. See FIG. 12. In a few cases there is (surgery-related) ischemic necrosis of superficial areas of the cerebral cortex.

The Tutoplast® Dura sample also displays an extensive inflammatory response, especially in the subarachnoidal space. The graft itself is not infiltrated by inflammatory cells, but inflammatory lymphocytes and monocytes and foreign body reaction are identifiable at both ends.

Figure 13:
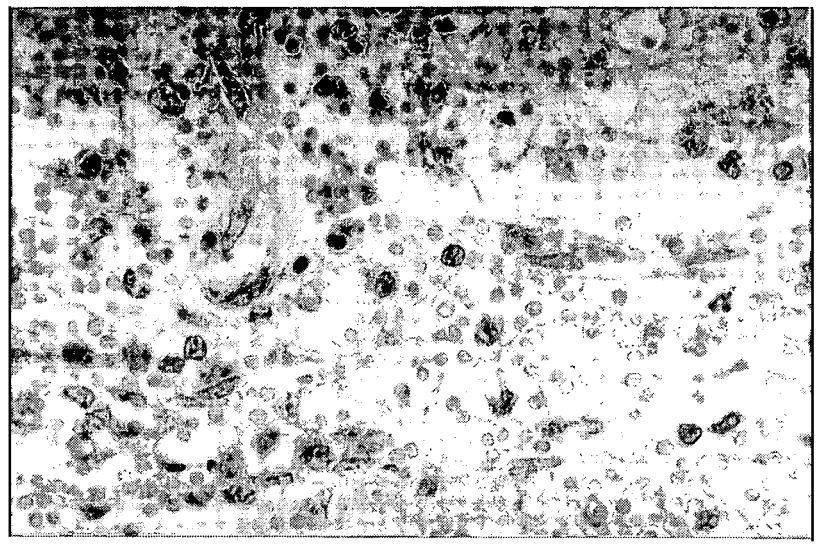
FIG. 13 is a photograph illustrating fibroblast and phagocytic cells that have infiltrated the equine collagen foil biomatrix graft, four weeks post-operation. Neocapillaries with erythrocytes are also visible (HE staining, 600× magnification).
Figure 14:
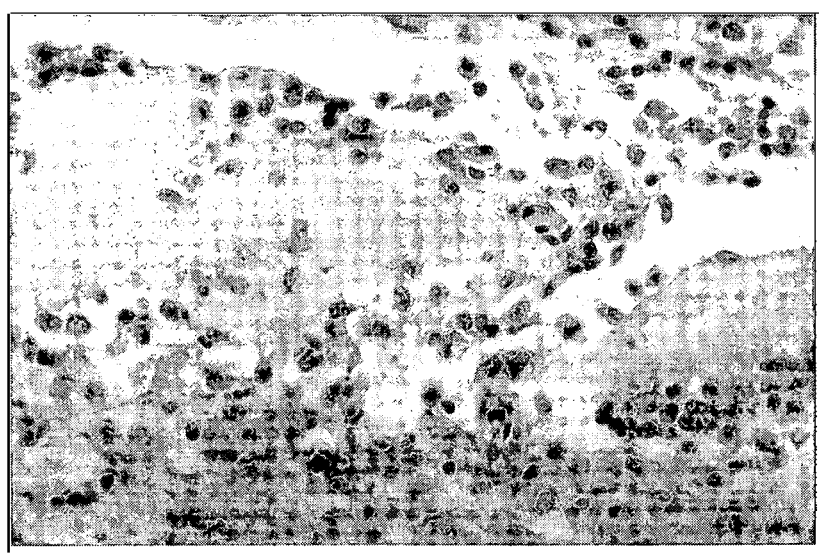
FIG. 14 is a photograph illustrating fragments of the equine collagen foil biomatrix graft that are surrounded by phagocytic cells and a mild lymphocytic inflammation, four weeks post-operation (HE staining, 600× magnification).

After a period of four weeks, inflammatory changes in the equine collagen foil graft site have regressed significantly, but lawn-like lymphocytic and monocytic exudates are still present. See FIGS. 13 and 14. Polynuclear foreign body giant cells are more common, especially near splinters of bone. Numerous fibroblasts can be seen within the original equine collagen foil graft. The typical homogenous structures of the graft are not detectable in the HE (hematoxillin-eosin-staining) sections. The samples stained with EVG (Elastica von Gieson) and trichrome show extensive neogenesis of collagen fibres at the former graft site. The actual dura mater smoothly gives way to loosely structured tissue consisting of newly formed collagen fibres displaying inflammatory infiltration. The previously observed inflammatory adhesion of the leptomeninges is no longer present. The subarachnoidal space is again in evidence, leaving a cleft. The pia mater continues to display small nodules of lymphocytic-monocytic infiltration in places.

Figure 15:
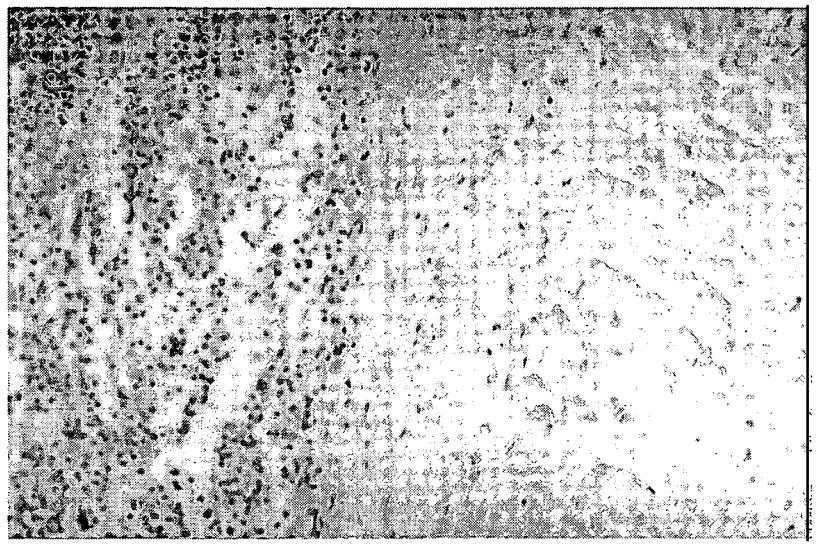
FIG. 15 is a photograph illustrating the Tutoplast® Dura cadaveric dura, four weeks post-operation. The cadaveric dura shows minimal signs of cellular infiltration or graft remodelling. A dense lymphocytic inflammatory reaction is found above and below the graft (HE staining, 250× magnification).

There are no signs of connective tissue organization at the Tutoplast® Dura site. Inflammatory exudation is present above and below the implanted tissue and inflammatory infiltrates are present in the zone of transition to the preformed dura. The subarachnoidal space is detectable and patent. See FIG. 15.

Figure 16:
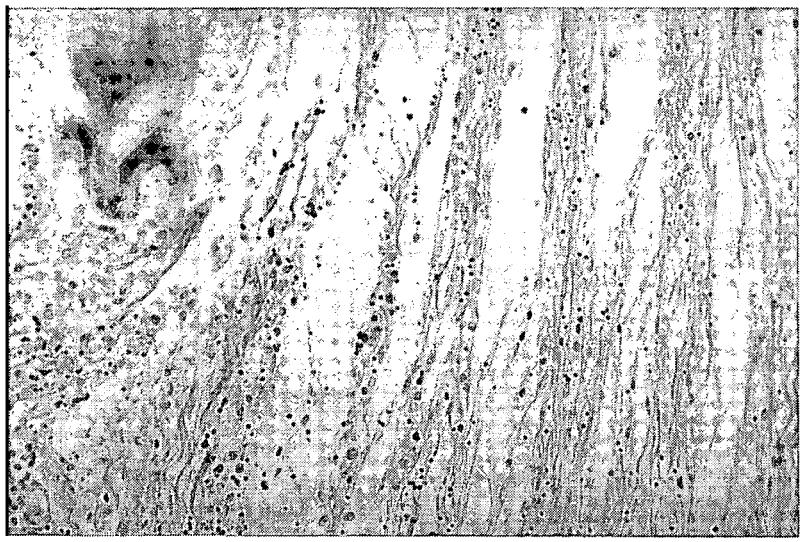
FIG. 16 is a photograph of a microscopic aspect of the neodura eight weeks post-operation illustrating newly formed layers of collagen fibres, fibroblasts, and residues of the equine collagen foil biomatrix graft (Trichrom staining, 150× magnification).

Eight weeks postoperatively, in the equine collagen foil group, inflammatory processes in the neodura have regressed further. Only small clusters of lymphocytic and monocytic infiltration are still present. The subarachnoidal space is clear and, again, only small foci of inflammatory activity are present. The sections stained with EVG and trichrome show marked continuity between the highly collagenous endogenous dura and the newly formed collagen fibres of the neodura. This new membrane appears to vary in thickness and displays structural loosening in parts. See FIG. 16.

Inflammatory activity has also cleared up well in the Tutoplast® Dura site. Incorporation with the neighbouring dura is absent in places and in others there are signs of inflammatory infiltration and adhesion with the adjacent dura.

After 16 weeks, in the equine collagen foil group, clusters of lymphocytic and monocytic nodular inflammatory infiltrates are still visible. The continuity between the highly collagenous actual dura and neodura is unchanged, with structures displaying no major changes versus the findings at 8 weeks. Collagen fibres of varying thickness are present, with some structural loosening in places.

The Tutoplast® Dura site again shows inflammatory changes and adhesions with the surrounding dura; these findings vary in intensity.

Figure 17:
FIG. 17 is a photograph of a microscopic aspect of the neodura sixteen weeks after implantation of the equine collagen foil illustrating dense collagen fibres and newly formed capillaries, filled with erythrocytes (van Gieson staining, 200× magnification).

After 24 weeks, in the equine collagen foil group, apart from further regression of the cellular inflammatory response, there are no relevant histological differences to the graft incorporation stage at 16 weeks. See FIG. 17.

Histology Results

Quantification of inflammatory response, connective tissue organization and extent of foreign body reaction in graft sites and subdural and epidural space are provided below in Table 1.

TABLE 1

| | | Examination of Grafts, Subdural and Epidural Space | | | | | |
|---|---|---|---|---|---|---|---|
| | | Equine collagen foil Graft, sub-/epidural space | | | TutoPlast ® Dura Graft, sub-/epidural space | | |
| Time | Animal | Inflammation | Organization | Foreign Body Reaction | Inflammation | Organization | Foreign Body Reaction |
| Week 2 | 1 | +++ | -- | + | ++ | -- | ++ |
| | 2 | +++ | -- | ++ | ++ | -- | + |
| | 3 | +++ | -- | +++ | ++ | -- | ++ |
| | 4 | +++ | -- | ++ | +++ | -- | +++ |
| | 5 | +++ | -- | +++ | ++ | -- | ++ |
| Week 4 | 6 | ++ | u | + | ++ | -- | + |
| | 7 | + | u | -- | + | -- | ++ |
| | 8 | + | u/K | -- | + | -- | + |
| | 9 | ++ | u | + | ++ | -- | + |
| | 10 | + | u/K | + | ++ | -- | + |
| Week 8 | 11 | + | K | + | ++ | -- | + |
| | 12 | + | K | + | -- | -- | -- |
| | 13 | ++ | K | u/+ | ++ | -- | + |
| | 14 | u/+ | K | -- | ++ | -- | + |
| | 15 | + | K | u | -- | -- | + |
| Week 16 | 16 | -- | K | -- | + | -- | -- |
| | 17 | -- | K | -- | + | -- | -- |
| | 18 | -- | K | -- | -- | -- | -- |
| | 19 | -- | K | -- | ++ | -- | -- |
| | 20 | -- | K | -- | + | -- | -- |
| Week 24 | 21 | -- | K | -- | + | -- | -- |
| | 22 | -- | K | -- | -- | -- | -- |
| | 23 | -- | K | -- | -- | -- | -- |
| | 24 | -- | K | -- | + | -- | -- |
| | 25 | -- | K | -- | -- | -- | -- |

Inflammation (Inflammatory reaction):
-- No visible signs of inflammatory response
u Circumscribed inflammatory infiltrates only
+ Mild inflammatory response
++ Significant inflammatory reaction
+++ Severe inflammatory infiltrates
Organization of graft:
-- Connective tissue organization absent or slight
+ Isolated fibroblasts within graft
u Circumscribed tissue organization (40%–70%)
u/K Tissue organization >70%
K Visible continuity of neodura and dura, full organization (100%) of the graft
Foreign body reaction with polynuclear giant cells:
-- No foreign body reaction
u Circumscribed foreign body reaction only
+ Mild foreign body reaction
++ Significant foreign body reaction
+++ Extensive foreign body reaction The histological examination results of the subarachnoidal space at both graft sites are provided in Table 2, below.

TABLE 2

Examination of the Subarachnoidal Space (SAS)

| Time | Animal | Equine collagen foil Subarachnoidal Space | | | TutoPlast ® Dura Subarachnoidal Space | | |
|---|---|---|---|---|---|---|---|
| | | Inflammation | Closed | Open | Inflammation | Closed | Open |
| Week 2 | 1 | + | + | -- | ++ | + | -- |
| | 2 | ++ | + | -- | ++ | + | -- |
| | 3 | +++ | + | -- | ++ | + | + |
| | 4 | +++ | + | -- | +++ | + | -- |
| | 5 | ++ | + | -- | ++ | + | + |
| Week 4 | 6 | -- | -- | + | + | -- | + |
| | 7 | -- | F | + | -- | F | + |
| | 8 | -- | F | + | -- | F | + |
| | 9 | + | F | + | + | F | + |
| | 10 | -- | -- | + | + | F | -- |
| | | | | | | F | |
| Week 8 | 11 | + | -- | + | -- | -- | + |
| | 12 | + | u | + | -- | -- | + |
| | 13 | -- | -- | + | -- | -- | + |
| | 14 | -- | u | + | -- | -- | + |
| | 15 | -- | -- | + | -- | -- | + |
| Week 16 | 16 | -- | F | -- | -- | F | -- |
| | 17 | -- | F | -- | -- | F | + |
| | 18 | -- | F | -- | -- | F | -- |
| | 19 | -- | F | -- | -- | F | -- |
| | 20 | -- | F | -- | -- | F | -- |
| Week 24 | 21 | -- | F | + | -- | F | + |
| | 22 | -- | F | + | -- | F | + |
| | 23 | -- | F | + | -- | F | + |
| | 24 | -- | F | + | -- | F | + |
| | 25 | -- | F | + | -- | F | + |

Inflammation:
-- No inflammatory response
+ Mild inflammatory reaction
++ Significant inflammatory response
Severe inflammatory reaction
SAS (subarachnoidal space) closed:
-- Scattered inflammatory cells
+ SAS closed by cellular infiltrate
u Isolated inflammatory infiltrates in SAS
pF/F Partial fibrosis/Fibrosis of SAS
SAS open:
-- SAS mainly clear with isolated cell groups
+ Subarachnoidal space clear Discussion Assessment of Surgical Methods and Handling of Both Grafts The equine collagen foil was characterized by problem-free intraoperative handling. Rehydration in physiological saline for 5 minutes produced an extremely tough approximately 2 mm thick film that did not lose its shape, did not conglutinate and was easy to cut to shape. The material was easy to position in the dural defect using forceps and a blunt hook. Owing to its mobility, it was also easy to correct the position of the equine collagen foil on the brain surface before fixing it in place. There was no need to suture the film because the graft was quickly and easily attached to the dural border using fibrin glue. Previous studies have also shown that fibrin glue is a reliable sealant for dural closure.

Experimentally administered holding sutures tore off the equine collagen foil at the slightest tug, indicating that fibrin glue is the better approach for this graft.

When the products were later removed, there was evidence in some cases that too liberal application of fibrin glue had led to adhesion with the overlying bone in places. These adhesions had to be loosened cautiously with a dissector to avoid pulling on the meninges and cortex. This problem was avoided by applying or dotting on sparing amounts of the fibrin glue. When the products were removed it was clear that application of fibrin glue on its own produces secure dural closure and prevents seepage of cerebrospinal fluid. This was apparent as early as 2 weeks postoperatively when none of the animals developed subcutaneous CSF leakage or cerebrospinal fluid fistulae.

The Tutoplast® Dura product is also easy to handle after a brief rehydration period of several minutes, but is much more rigid and displays great fluctuation in terms of calibre.

Fibrin glue produced adequate adhesion to keep the Tutoplast® Dura in place initially, but the connection between the original dura and graft was loose when the surgical site was reopened. This was still the case at postoperative week 24 due to the fact that the Tutoplast® Dura itself had not fused with the autologous dura mater. The practice of attaching this graft with individual sutures therefore seems to be superior to the use of fibrin glue as observations indicate that adequate incorporation will not otherwise occur. There were very rare adhesions in the transitional zone between Tutoplast® Dura and cortex which were easy to loosen using a dissector.

The technique used for inserting the equine collagen foil between the dura and the cortex is likely to be unsuitable in certain surgical situations. In particular, adequate fixation is unlikely to be achieved with this method in procedures involving large defects of the cerebral parenchyma, for example, tumor cavities.

Macroscopically, all the animals displayed reliable closure of the dural defect with no graft rejection reactions. Small adhesions between the implant and cortical structures developed in a few cases, probably due to tiny injuries to the arachnoidea mater during surgery. Overly liberal use of fibrin glue resulted in some animals in small areas of adhesion with the overlying bone which were easily loosened.

Histologically, dense infiltration of the equine collagen foil with lymphocytes, macrophages and fibroblasts was seen within 14 days after implantation. Capillaries form in the graft later in time. Concomitant inflammatory changes in the subarachnoidal and subdural/epidural space and in the dura-graft transitional zone were regressing well just 4 weeks postoperatively. A continuous transition between the equine collagen foil graft and surrounding dura due to the neogenesis of collagen fibres is also evident at this point in time.

This neodura that was induced by the equine collagen foil is not as thick as the original dura at postoperative week 24, probably because the dura mater foil provided only a certain thickness from the outset. It is possible however that this difference is offset later on as more collagen fibres are produced.

At two weeks postoperatively, the Tutoplast® Dura displays macroscopically visible encapsulation of the product in a thin layer of connective tissue which becomes thicker as time continues. Again, all animals display adequate dural closure with no CSF fistulae, and a few adhesions between the graft and cortex or bone are present.

In spite of similar inflammatory reactions in the structures surrounding the graft, there are no signs of postoperative organization processes and little evidence of cellular infiltration and revitalization of the graft.

None of the animals developed neurological abnormalities or wound infections apart from an intended locally contained lymphocytic and monocytic inflammatory response.

Example 2

Swelling Capacity of Equine Collagen Foil

The investigations concerning the swelling capacity of the equine collagen foil were carried out as follows:

1) The equine collagen foil was first cut into 1 cm quadratic pieces.
2) Samples of these cut pieces were examined under a conventional scanning microscope to determine the gross morphologic consistency and the thickness of the material as a reference for the swelling procedures.
3) These pieces were then brought into plastic culture dishes.
4) The capacity of fluid uptake and swelling capacity was then examined by successive titration with physiologic saline solution, administered with Eppendorf micropipettes using ascending amounts of fluid, starting with 10 µl/cm$^2$ up to 150 µl/cm$^2$ (see Table 3).

TABLE 3

| | Amount of Fluid Administered to the Equine Collagen Foil | | | | | | | | |
|---|---|---|---|---|---|---|---|---|---|
| Time | 10 µl/cm$^2$ | 20 µl/cm$^2$ | 30 µl/cm$^2$ | 40 µl/cm$^2$ | 50 µl/cm$^2$ | 75 µl/cm$^2$ | 100 µl/cm$^2$ | 125 µl/cm$^2$ | 150 µl/cm$^2$ |
| 1 Hr | No swelling effect | Fluid completely soaked into material, no supernatant after 1 hour | Fluid completely soaked into material, no supernatant after 1 hour | Fluid completely soaked into material, no supernatant after 1 hour | 10 µl supernatant | 25 µl supernatant | 50 µl supernatant | 75 µl supernatant | 100 µl supernatant |
| 2 Hrs | No swelling effect | Fluid completely soaked into material, no supernatant after 2 hours | Fluid completely soaked into material, no supernatant after 2 hours | Fluid completely soaked into material, no supernatant after 2 hours | 10 µl supernatant | 25 µl supernatant | 50 µl supernatant | 75 µl supernatant | 100 µl supernatant |
| 3 Hrs | No swelling effect | Fluid completely soaked into material, no supernatant after 3 hours | Fluid completely soaked into material, no supernatant after 3 hours | Fluid completely soaked into material, no supernatant after 3 hours | 10 µl supernatant | 25 µl supernatant | 50 µl supernatant | 75 µl supernatant | 100 µl supernatant |

Results:

the amount of fluid that was soaked into the equine collagen foil was determined after 1, 2, and 3 hours as listed above.

A piece of equine collagen foil material measuring 1 cm$^2$ absorbed 10 µl amount of saline fluid completely without a significant visible swelling of the thickness.

An amount of 20 µl of saline fluid was completely absorbed by the 1 cm$^2$ piece of equine collagen foil and led to a slight increase in the thickness of the material.

Only a minimal increase of equine collagen foil thickness was observed in the whole series. It is estimated that the maximum increase in thickness is only about double the initial volume, even after 3 hours.

No significant increases in thickness or absorption of fluid were observed after the first hour.

Example 3

Increase of Length of Hydrated Equine Collagen Foil

Seven dry pieces of equine collagen foil measuring 1.0 cm$^2$ were hydrated for 1 hour in isotonic sodium chloride. The average length extension resulting from hydration of dry pieces of equine collagen foil was approximately 3.4 percent.

TABLE 4

| Piece No. | Length Dry (mm) | Length Hydrated (mm) |
|---|---|---|
| 1 | 17.5 | 18 |
| 2 | 17.7 | 18.3 |
| 3 | 17 | 17.9 |
| 4 | 17.8 | 18.5 |
| 5 | 18.1 | 18.7 |
| 6 | 18.6 | 19.5 |
| 7 | 17.7 | 18.2 |
| Average | 17.8 | 18.4 |

Example 4

Increase in Weight of Hydrated Equine Collagen Foil

Seven dry pieces of equine collagen foil measuring 1.0 cm² were hydrated in isotonic sodium chloride for 1 hour. The hydrated pieces of equine collagen foil weighed about five times more than when in a dry state.

TABLE 5

| Piece No. | Dry Weight (mg) | Hydrated Weight (mg) |
|---|---|---|
| 1 | 8.4 | 40.2 |
| 2 | 7.6 | 37.9 |
| 3 | 8 | 39.3 |
| 4 | 8.1 | 39.6 |
| 5 | 8.6 | 41.9 |
| 6 | 8.7 | 46.8 |
| 7 | 7.7 | 38.3 |
| Average | 8.2 | 40.6 |

Example 5

Tensile Strength and Elasticity/Flexibility of Equine Collagen Foil

Figure 18:
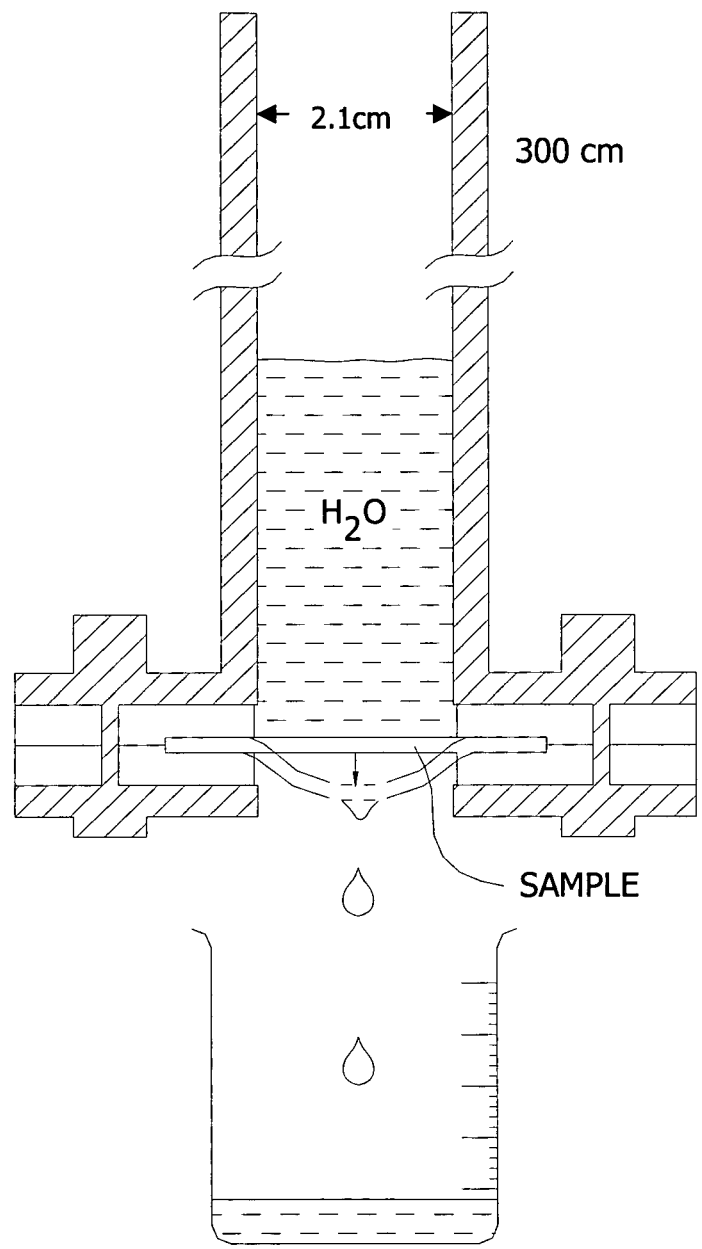
FIG. 18 is a drawing illustrating the test apparatus utilized to measure water-tightness, tensile strength and elasticity/flexibility of replacement dura mater material. The extent of convexity of the material that resulted from a specific water column height was measured to determine the level of elasticity/flexibility. The amount of water, pressed through the test materials, was measured to test water-tightness.

The tensile strength of several dura mater products and the equine collagen foil of the present invention were measured. The samples were mounted at the lower end of a tube and the tensile strength was increased by a continuously growing column of water up to a maximum of 300 cm. FIG. 18 provides an illustration of the test chamber.

The test chamber was able to determine the strength of the dura mater substitute products by identifying the point at which a product would fail due to pressure that exceeded the product's tensile strength. The equine collagen foil (collagen content: 5.6 mg/cm²) of the present invention and a collagen foil (collagen content: 4.0 mg/cm) were compared to Duragen (Integra NeuroSciences, Plainsboro, N.J.).

Figure 19:
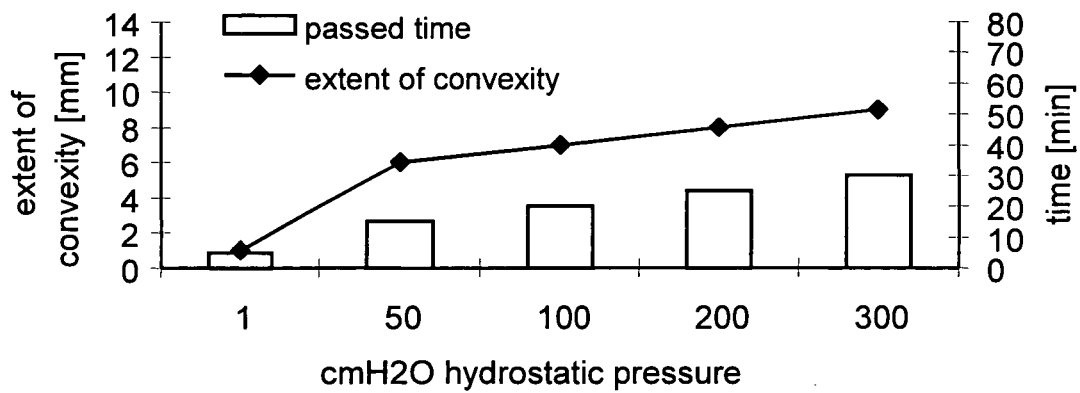
FIG. 19 is a graph depicting the extent of convexity of equine collagen foil (collagen content: 5.6 mg/cm$^2$) over increased hydrostatic pressure (water column heights).
Figure 20:
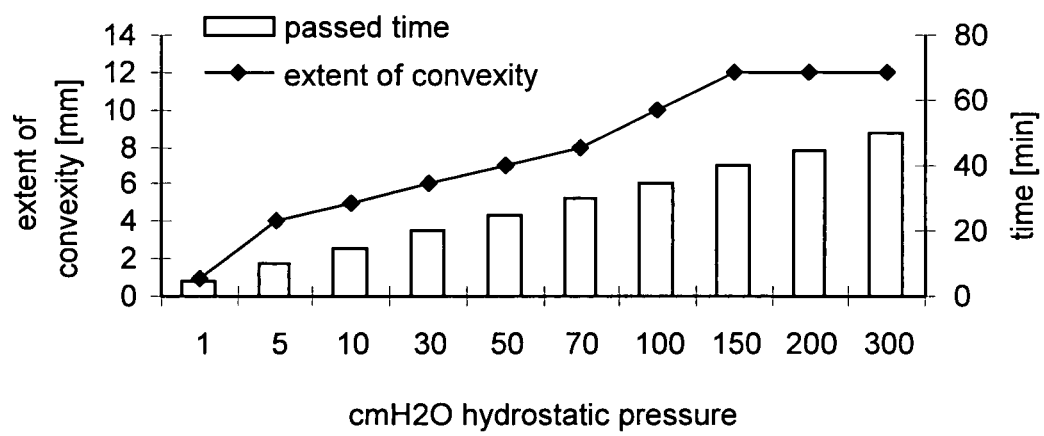
FIG. 20 is a graph depicting the extent of convexity of a collagen foil (collagen content: 4 mg/cm$^2$) over increased hydrostatic pressure (water column heights).

The test results indicated that the equine collagen foil (collagen content: 5.6 mg/cm²) and the collagen foil (collagen content: 4.0 mg/cm²) withstood up to a 300 cm column of water without failing. See FIGS. 19 and 20. In comparison, the pressure exerted in the healthy skull does not exceed more than approximately 15 cm high water column; in pathologic situations, the pressure can rise up to approximately 50 cm.

Figure 21:
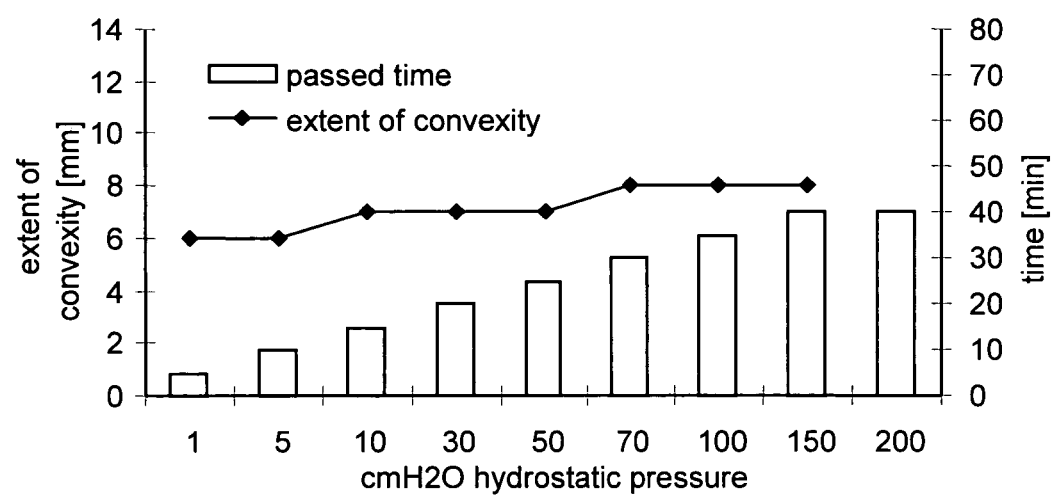
FIG. 21 is a graph depicting the extent of convexity of DuraGen over increased hydrostatic pressure (water column heights). DuraGen ruptured at 200 cm H$_2$O hydrostatic pressure.
Figure 22:
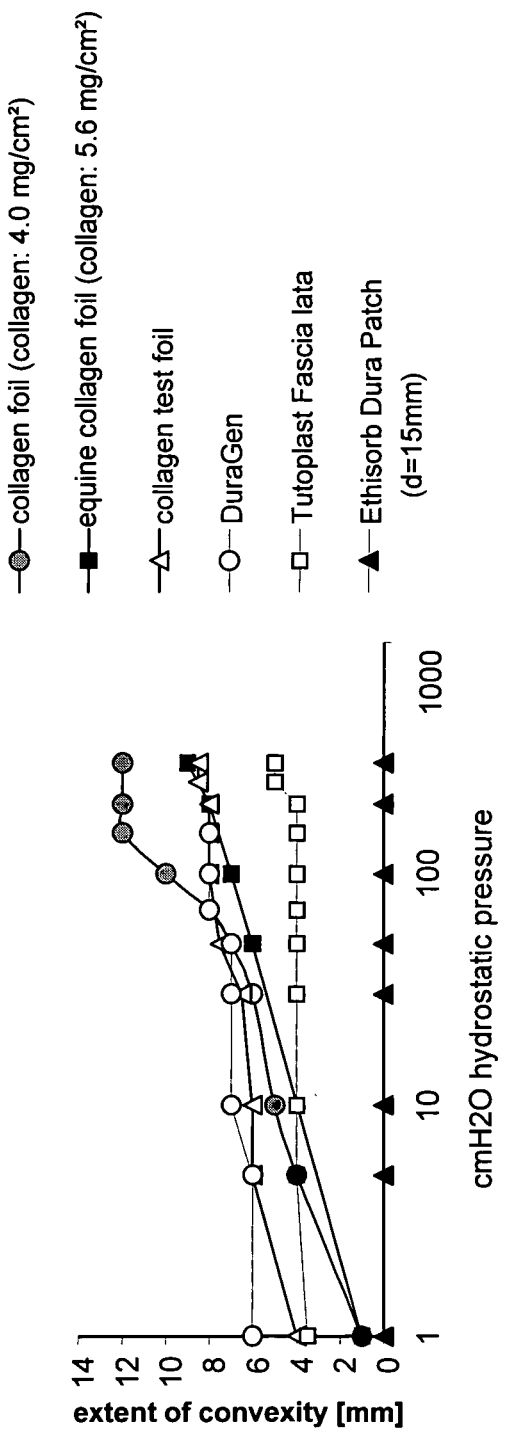
FIG. 22 is a graph depicting the extent of convexity of several dura mater replacement products over increased hydrostatic pressure (water column heights).
Figure 23:
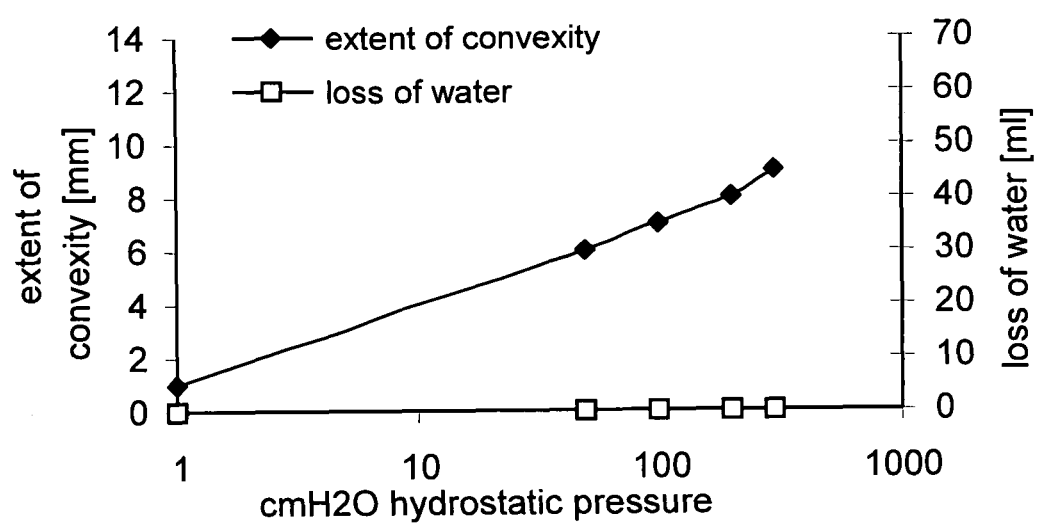
FIG. 23 is a graph depicting the extent of convexity and loss of water of equine collagen foil (collagen content: 5.6 mg/cm$^2$) over increased hydrostatic pressure (water column heights).
Figure 24:
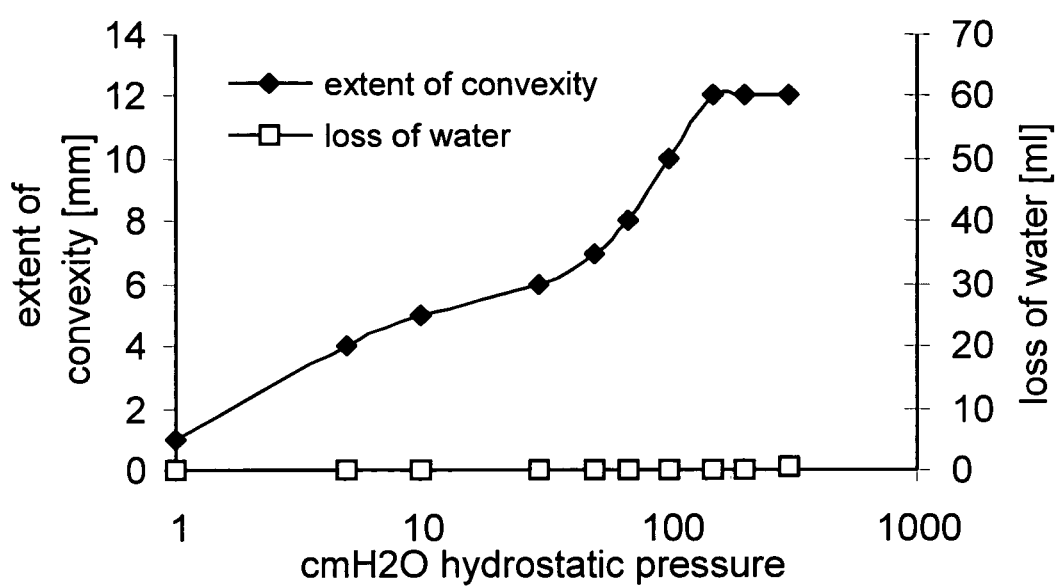
FIG. 24 is a graph depicting the extent of convexity and loss of water of a collagen foil (collagen content: 4 mg/cm$^2$) over increased hydrostatic pressure (water column heights).
Figure 25:
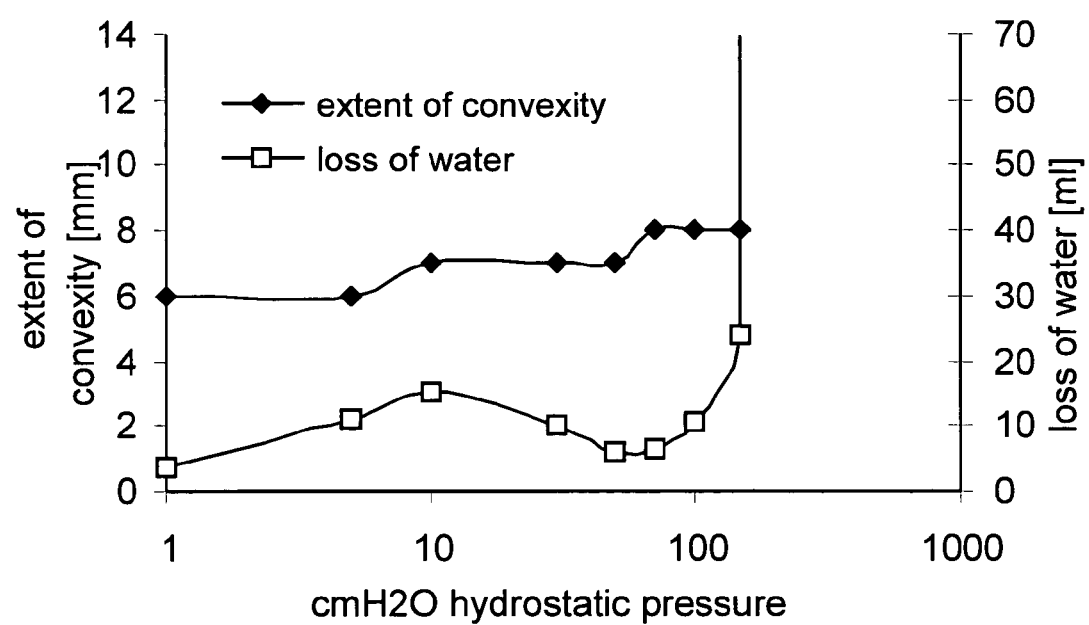
FIG. 25 is a graph depicting the extent of convexity and loss of water of DuraGen over increased hydrostatic pressure (water column heights).
Figure 26:
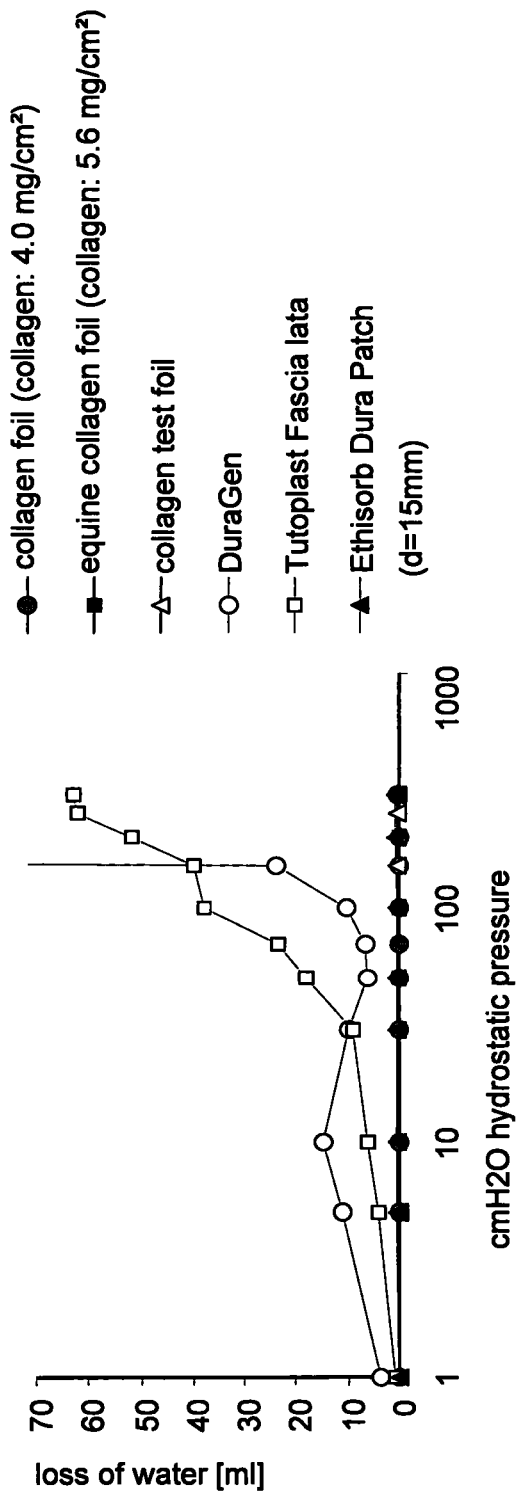
FIG. 26 is a graph depicting the extent of convexity and loss of water of several dura mater replacement products over increased hydrostatic pressure (water column heights).

DuraGen measured significantly lower tensile strength, bursting under the pressure of a 200 cm water column. See FIG. 21.

The test chamber was also able to compare the elasticity of the products by identifying the extent at which the product would stretch under the pressure. The elasticity/flexibility of a product was therefore determined by measuring the convexity of the product under the weight of the water column.

The elasticity/flexibility of the equine collagen foil (collagen content: 5.6 mg/cm²) and the collagen foil (collagen content: 4.0 mg/cm²) were compared to DuraGen, a collagen test foil, Tutoplast Fascia lata (Tutogen Medical GmbH, Neunkirchen am Brand, Germany), and Ethisorb Dura Patch (Ethicon GmbH & Co. KG, Nordrstedt. Germany). See FIGS. 22-25.

In comparison to the other products, the equine collagen foil (collagen content: 5.6 mg/cm²) displayed a mixture of significant tensile strength coupled with elasticity/flexibility. This permits it to withstand the pressure exerted against it as a dura mater substitute while remaining flexible and elastic, allowing it to form to the contours of the brain and cranium. In contrast, Ethisorb and Tutoplast, displayed high tensile strength in the water column experiment but possessed much lower elasticity/flexibility.

Example 6

Liquid-Tight Properties

Measurements of liquid-tight properties of replacement dura mater products were determined using the same experimental setup as was discussed in Example 5.

In this experiment, the development of drops of water and the volume of lost water was measured in relation to the height of the water column. The results of this experiment are illustrated in FIGS. 23-26.

In this experiment, the equine collagen foil (collagen content: 5.6 mg/cm²) remained liquid-tight while under more than a 300 cm high water column. The collagen foil (collagen content: 4.0 mg/cm²) displayed a loss of fine water drops under a 300 cm high water column. Having a porous structure, DuraGen was not water-tight, but displayed clearly visible loss of water under even low water pressures. Similarly, Tutoplast Fascia Lata was also not water-tight, displaying a loss of water under low pressures.

Example 7

Stability and Tear Resistance

Only materials that are sufficiently stable, elastic, and tear resistant in wet and dry environment are suitable as implants in special surgical situations, such as for substitute dura maters. Determination of tear resistance/ultimate tensile force of the moistened material therefore provides valuable information with respect to structure, stability, and likelihood of remaining in place at the surgical site.

The tear resistance of collagenous surgical implants was tested on hydrated specimen in order to mimic the conditions prevailing in the body. The materials were placed in isotonic saline solution for five minutes.

To measure the tear resistance/ultimate tensile force, strips of collagenous implants were clamped into a Zwick Model 1120 All-Purpose Testing Machine (Zwick GmbH & Co. KG, Ulm, Germany). The tested collagenous implants are provided in Table 6.

TABLE 6

| Collagenous Implants | | | |
|---|---|---|---|
| Strip | Agent | Concentration | Origin |
| A | Collagen "Compress" Sponge | 10.0 mg/cm² | Bovine Corium |

TABLE 6-continued

Collagenous Implants

| Strip | Agent | Concentration | Origin |
|---|---|---|---|
| B | Collagen "Foam" Sponge | approx. 2.6 mg/cm² | Equine Achilles Tendon |
| C | Collagen Sponge | 2.8 mg/cm² | Equine Achilles Tendon |
| D | Collagen Foil | 4.0 mg/cm² | Equine Achilles Tendon |
| E | Equine collagen Foil | 5.6 mg/cm² | Equine Achilles Tendon |

Figure 27:
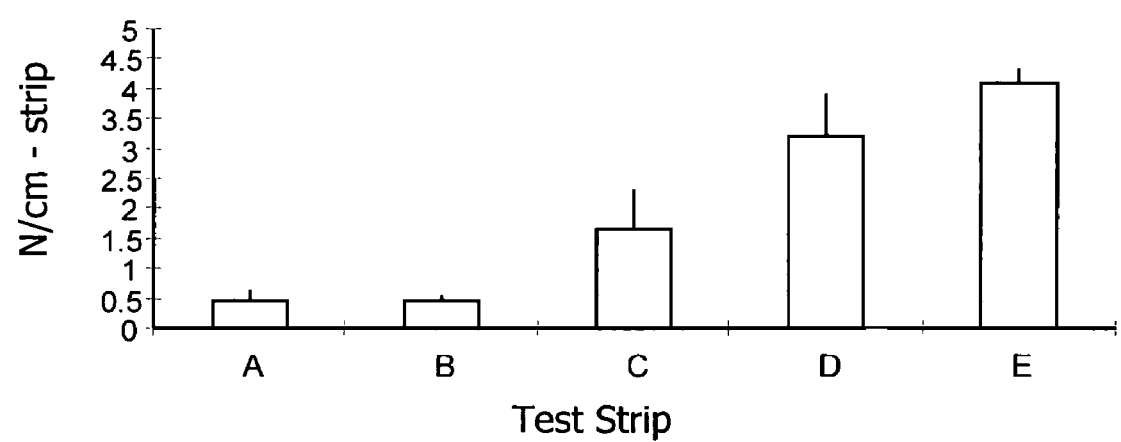
FIG. 27 is a graph depicting the tear resistance/ultimate tensile force of various collagenous implants. Sample E is equine collagen foil.

Machine control, data acquisition, and testing, including statistical evaluation, were performed using TestExpert software (Zwick GmbH & Co. KG, Ulm, Germany). Test sponge specimens A, B, and C seemed to be rather fragile. Specimens A, B, and C were cut into 4 cm strips having a width of 1.4 cm. The test results of all specimens were calculated proportionally for a strip of 1.0 cm width. The ultimate tensile force values of test strips were measured in Newtons/cm-strip. The test results are provided in Table 7 and FIG. 27.

TABLE 7

Tear Resistance/Ultimate Tensile Force

| | Tear Resistance/ Ultimate Tensile Force (Newtons/cm-strip) | Standard Deviation |
|---|---|---|
| A | 0.46 | 0.19 |
| B | 0.45 | 0.11 |
| C | 1.64 | 0.69 |
| D | 3.21 | 0.69 |
| E | 4.09 | 0.24 |

CONCLUSIONS

The unique fabrication method of the equine collagen foil increases its tear resistance/ultimate tensile force.

Collagenous foils displayed significantly higher tear resistance/ultimate tensile force compared to collagenous sponges.

The tear resistance of collagenous foils increased with the collagen content per square centimeter (e.g., Collagen content of 4.0 mg/cm²: 3.21 N/cm-strip; Collagen content of 5.6 mg/cm²: 4.09 N/cm-strip).

In view of the above, it will be seen that the several objects of the invention are achieved.

As various changes could be made in the above compositions and processes without departing from the scope of the invention, it is intended that all matter contained in the above description be interpreted as illustrative and not in a limiting sense.

With reference to the use of the word(s) "comprise" or "comprises" or "comprising" in this entire specification (including the claims below), Applicants note that unless the context requires otherwise, those words are used on the basis and clear understanding that they are to be interpreted inclusively, rather than exclusively, and that Applicants intend each of those words to be so interpreted in construing this entire specification.

The invention claimed is:

1. A method of repairing and regenerating dura mater tissue in a mammal comprising attaching a collagen foil to the dura matter tissue, wherein the collagen foil comprises a non-naturally occurring biomatrix of multiple layers of precipitated collagen fibrils having a diameter of between 10 to 300 nanometers that are not cross-linked by chemicals or radiation, wherein the biomatrix comprises pores that are isolated from one another and are not interconnected in a manner which traverses the collagen foil, wherein the multiple layers of precipitated collagen fibrils form stacked collagen fibril sheets packed tightly together with interstices there between, and wherein the multiple layers of precipitated collagen fibrils of the collagen foil have an ultimate tensile force of between 0.5 Newtons/cm-strip and 30 Newtons/cm-strip.

2. The method of claim 1, wherein the collagen foil is an equine collagen foil.

3. The method of claim 2, wherein the collagen fibrils are derived from tendons.

4. The method of claim 2, wherein the dura mater tissue is located in the cranium.

5. The method of claim 2, wherein the dura mater tissue is located in the spinal column.

6. The method of claim 2, wherein the attaching step comprises one or more methods selected from the group consisting of: attaching the collagen foil to the dura mater tissue with fibrin sealant, attaching the collagen foil to the dura mater tissue with tissue glue, attaching the collagen foil to the dura mater tissue with surgical sutures, attaching the collagen foil to the dura mater tissue utilizing pressure fitting techniques, and attaching the collagen foil to the dura mater tissue utilizing natural adhesion between the collagen foil and the dura matter tissue.

7. The method of claim 2, wherein the collagen foil is substantially liquid tight.

8. The method of claim 2, wherein the collagen foil does not adhere to neural tissue or brain tissue after cell organization of the collagen foil with meningeal cells.

9. The method of claim 2, wherein the collagen foil does not adhere to the skull or spinal column tissue after cell organization of the collagen foil with meningeal cells.

10. The method of claim 2, wherein the mammal is selected from the group consisting of humans, horses, sheep, monkeys, and laboratory animals.

11. The method of claim 2, wherein the collagen foil further comprises an excipient selected from the group consisting of a preservative, a growth factor, an additive that aids in the flexibility and elasticity of the collagen foil, and combinations thereof.

12. A method of repairing and regenerating dura mater tissue in a mammal comprising attaching a collagen foil to the dura matter tissue, wherein the collagen foil comprises a non-naturally occurring biomatrix of multiple layers of precipitated collagen fibrils, wherein the biomatrix comprises pores that are isolated from one another and are not interconnected in a manner which traverses the collagen foil, wherein the multiple layers of precipitated collagen fibrils form stacked collagen fibril sheets packed tightly together with interstices there between, and wherein the multiple layers of precipitated collagen fibrils of the collagen foil have an ultimate tensile force of between 0.5 Newtons/cm-strip and 30 Newtons/cm-strip.

13. The method of claim 12, wherein the multiple layers of precipitated collagen fibrils of the collagen foil have an ultimate tensile force of between 1 Newtons/cm-strip and 6 Newtons/cm-strip.

14. The method of claim 12, wherein the dura mater tissue is located in the cranium.

15. The method of claim 12, wherein the dura mater tissue is located in the spinal column.

16. The method of claim 12, wherein the attaching step comprises one or more methods selected from the group consisting of: attaching the collagen foil to the dura mater tissue with fibrin sealant, attaching the collagen foil to the dura mater tissue with tissue glue, attaching the collagen foil to the dura mater tissue with surgical sutures, attaching the collagen foil to the dura mater tissue utilizing pressure fitting techniques, and attaching the collagen foil to the dura mater tissue utilizing natural adhesion between the collagen foil and the dura matter tissue.

17. The method of claim 12, wherein the collagen foil is substantially liquid tight.

18. The method of claim 12, wherein the collagen foil does not adhere to neural tissue or brain tissue after cell organization of the collagen foil with meningeal cells.

19. The method of claim 12, wherein the collagen foil does not adhere to the skull or spinal column tissue after cell organization of the collagen foil with meningeal cells.

20. The method of claim 12, wherein the mammal is selected from the group consisting of humans, horses, sheep, monkeys, and laboratory animals.

21. The method of claim 12, wherein the collagen foil further comprises an excipient selected from the group consisting of a preservative, a growth factor, an additive that aids in the flexibility and elasticity of the collagen foil, and combinations thereof.

22. The method of claim 1, wherein the collagen foil, in its dry form, has a thickness of between 0.01 mm and 3.0 mm.

23. The method of claim 22, wherein the collagen foil, in its dry form, has a thickness of between 0.03 mm and 1.5 mm.

24. The method of claim 22, wherein the dura mater tissue is located in the cranium.

25. The method of claim 22, wherein the dura mater tissue is located in the spinal column.

26. The method of claim 22, wherein the attaching step comprises one or more methods selected from the group consisting of: attaching the collagen foil to the dura mater tissue with fibrin sealant, attaching the collagen foil to the dura mater tissue with tissue glue, attaching the collagen foil to the dura mater tissue with surgical sutures, attaching the collagen foil to the dura mater tissue utilizing pressure fitting techniques, and attaching the collagen foil to the dura mater tissue utilizing natural adhesion between the collagen foil and the dura matter tissue.

27. The method of claim 22, wherein the collagen foil is substantially liquid tight.

28. The method of claim 22, wherein the collagen foil does not adhere to neural tissue or brain tissue after cell organization of the collagen foil with meningeal cells.

29. The method of claim 22, wherein the collagen foil does not adhere to the skull or spinal column tissue after cell organization of the collagen foil with meningeal cells.

30. The method of claim 22, wherein the mammal is selected from the group consisting of humans, horses, sheep, monkeys, and laboratory animals.

31. The method of claim 22, wherein the collagen foil further comprises an excipient selected from the group consisting of a preservative, a growth factor, an additive that aids in the flexibility and elasticity of the collagen foil, and combinations thereof.

32. The method of claim 1, wherein the collagen foil, in its dry form, has a thickness of 1.0 mm or less.

33. The method of claim 32, wherein the dura mater tissue is located in the cranium.

34. The method of claim 32, wherein the dura mater tissue is located in the spinal column.

35. The method of claim 32, wherein the attaching step comprises one or more methods selected from the group consisting of: attaching the collagen foil to the dura mater tissue with fibrin sealant, attaching the collagen foil to the dura mater tissue with tissue glue, attaching the collagen foil to the dura mater tissue with surgical sutures, attaching the collagen foil to the dura mater tissue utilizing pressure fitting techniques, and attaching the collagen foil to the dura mater tissue utilizing natural adhesion between the collagen foil and the dura matter tissue.

36. The method of claim 32, wherein the collagen foil is substantially liquid tight.

37. The method of claim 32, wherein the collagen foil does not adhere to neural tissue or brain tissue after cell organization of the collagen foil with meningeal cells.

38. The method of claim 32, wherein the collagen foil does not adhere to the skull or spinal column tissue after cell organization of the collagen foil with meningeal cells.

39. The method of claim 32, wherein the mammal is selected from the group consisting of humans, horses, sheep, monkeys, and laboratory animals.

40. The method of claim 32, wherein the collagen foil further comprises an excipient selected from the group consisting of a preservative, a growth factor, an additive that aids in the flexibility and elasticity of the collagen foil, and combinations thereof.

41. The method of claim 1, wherein the collagen foil, when completely hydrated, weighs up to 10 times its dry weight.

42. The method of claim 41, wherein the collagen foil, when completely hydrated, weighs up to 5 times its dry weight.

43. The method of claim 41, wherein the dura mater tissue is located in the cranium.

44. The method of claim 41, wherein the dura mater tissue is located in the spinal column.

45. The method of claim 41, wherein the attaching step comprises one or more methods selected from the group consisting of: attaching the collagen foil to the dura mater tissue with fibrin sealant, attaching the collagen foil to the dura mater tissue with tissue glue, attaching the collagen foil to the dura mater tissue with surgical sutures, attaching the collagen foil to the dura mater tissue utilizing pressure fitting techniques, and attaching the collagen foil to the dura mater tissue utilizing natural adhesion between the collagen foil and the dura matter tissue.

46. The method of claim 41, wherein the collagen foil is substantially liquid tight.

47. The method of claim 41, wherein the collagen foil does not adhere to neural tissue or brain tissue after cell organization of the collagen foil with meningeal cells.

48. The method of claim 41, wherein the collagen foil does not adhere to the skull or spinal column tissue after cell organization of the collagen foil with meningeal cells.

49. The method of claim 41, wherein the mammal is selected from the group consisting of humans, horses, sheep, monkeys, and laboratory animals.

50. The method of claim 41, wherein the collagen foil further comprises an excipient selected from the group consisting of a preservative, a growth factor, an additive that aids in the flexibility and elasticity of the collagen foil, and combinations thereof.

51. The method of claim 1, wherein the surface area of the collagen foil, when completely hydrated, is between −5% to 10% greater than when in its dry form.

52. The method of claim 51, wherein the surface area of the collagen foil, when completely hydrated, is up to about 4 percent greater than when in its dry form.

53. The method of claim 51, wherein the dura mater tissue is located in the cranium.

54. The method of claim 51, wherein the dura mater tissue is located in the spinal column.

55. The method of claim 51, wherein the attaching step comprises one or more methods selected from the group consisting of: attaching the collagen foil to the dura mater tissue with fibrin sealant, attaching the collagen foil to the dura mater tissue with tissue glue, attaching the collagen foil to the dura mater tissue with surgical sutures, attaching the collagen foil to the dura mater tissue utilizing pressure fitting techniques, and attaching the collagen foil to the dura mater tissue utilizing natural adhesion between the collagen foil and the dura matter tissue.

56. The method of claim 51, wherein the collagen foil is substantially liquid tight.

57. The method of claim 51, wherein the collagen foil does not adhere to neural tissue or brain tissue after cell organization of the collagen foil with meningeal cells.

58. The method of claim 51, wherein the collagen foil does not adhere to the skull or spinal column tissue after cell organization of the collagen foil with meningeal cells.

59. The method of claim 51, wherein the mammal is selected from the group consisting of humans, horses, sheep, monkeys, and laboratory animals.

60. The method of claim 51, wherein the collagen foil further comprises an excipient selected from the group consisting of a preservative, a growth factor, an additive that aids in the flexibility and elasticity of the collagen foil, and combinations thereof.

61. The method of claim 1, wherein the thickness of the collagen foil, when completely hydrated, is about twice the thickness of its dry form.

62. The method of claim 61, wherein the dura mater tissue is located in the cranium.

63. The method of claim 61, wherein the dura mater tissue is located in the spinal column.

64. The method of claim 61, wherein the attaching step comprises one or more methods selected from the group consisting of: attaching the collagen foil to the dura mater tissue with fibrin sealant, attaching the collagen foil to the dura mater tissue with tissue glue, attaching the collagen foil to the dura mater tissue with surgical sutures, attaching the collagen foil to the dura mater tissue utilizing pressure fitting techniques, and attaching the collagen foil to the dura mater tissue utilizing natural adhesion between the collagen foil and the dura matter tissue.

65. The method of claim 61, wherein the collagen foil is substantially liquid tight.

66. The method of claim 61, wherein the collagen foil does not adhere to neural tissue or brain tissue after cell organization of the collagen foil with meningeal cells.

67. The method of claim 61, wherein the collagen foil does not adhere to the skull or spinal column tissue after cell organization of the collagen foil with meningeal cells.

68. The method of claim 61, wherein the mammal is selected from the group consisting of humans, horses, sheep, monkeys, and laboratory animals.

69. The method of claim 61, wherein the collagen foil further comprises an excipient selected from the group consisting of a preservative, a growth factor, an additive that aids in the flexibility and elasticity of the collagen foil, and combinations thereof.

70. A method of repairing and regenerating dura mater tissue in a mammal comprising contacting a collagen foil to the dura matter tissue and allowing the collagen foil to be held in place in a desired implantation site by a natural adhesion that occurs between the collagen foil and the dura mater tissues, wherein the collagen foil comprises a non-naturally occurring biomatrix of multiple layers of precipitated collagen fibrils, wherein the biomatrix comprises pores that are isolated from one another and are not interconnected in a manner which traverses the collagen foil, wherein the multiple layers of precipitated collagen fibrils form stacked collagen fibril sheets packed tightly together with interstices there between.

71. The method of claim 70, wherein the contacting step comprises attaching the collagen foil to the dura mater tissue with a fibrin sealant.

72. The method of claim 70, wherein the contacting step comprises attaching the collagen foil to the dura mater tissue with a tissue glue.

73. The method of claim 70, wherein the contacting step comprises attaching the collagen foil to the dura mater tissue with surgical sutures.

74. The method of claim 70, wherein the contacting step comprises utilizing natural adhesion between the collagen foil and the dura mater tissue.

75. The method of claim 1, wherein the precipitated collagen fibrils are precipitated from a collagen suspension, and wherein the precipitation is caused at least in part due to raising the pH of the suspension.

76. The method of claim 1, wherein the collagen foil comprises a water content of between about 2% and 18% by weight.

77. The method of claim 1, wherein the collagen foil promotes cell and vasculature ingrowth across the foil through the interstices between the layers of collagen fibrils to form a neodura tissue in the mammal.

* * * * *

UNITED STATES PATENT AND TRADEMARK OFFICE
CERTIFICATE OF CORRECTION

PATENT NO. : 8,834,864 B2  Page 1 of 1
APPLICATION NO. : 11/291336
DATED : September 16, 2014
INVENTOR(S) : Johann Odar et al.

It is certified that error appears in the above-identified patent and that said Letters Patent is hereby corrected as shown below:

In the Claims

Column 30, Claim 6, line 28, please replace "matter" with -- mater --; and
Claim 11, line 47, please replace "matter" with -- mater --.

Column 31, Claim 16, line 8, please replace "matter" with -- mater --; and
Claim 26, line 42, please replace "matter" with -- mater --.

Column 32, Claim 35, line 7, please replace "matter" with -- mater --; and
Claim 45, line 43, please replace "matter" with -- mater --.

Column 33, Claim 55, line 12, please replace "matter" with -- mater --; and
Claim 64, line 45, please replace "matter" with -- mater --.

Column 34, Claim 70, line 14, please replace "matter" with -- mater --.

Signed and Sealed this
Twenty-seventh Day of January, 2015

Michelle K. Lee
*Deputy Director of the United States Patent and Trademark Office*